US009469649B2

(12) United States Patent
Moriarty

(10) Patent No.: US 9,469,649 B2
(45) Date of Patent: Oct. 18, 2016

(54) SYNTHETIC VOACANGINE

(71) Applicant: DemeRx, Inc., Fort Lauderdale, FL (US)

(72) Inventor: Robert M. Moriarty, Michiana Shores, IN (US)

(73) Assignee: DEMERX, INC., Fort Lauderdale, FL (US)

(*) Notice: Subject to any disclaimer, the term of this patent is extended or adjusted under 35 U.S.C. 154(b) by 104 days.

(21) Appl. No.: 14/506,505

(22) Filed: Oct. 3, 2014

(65) Prior Publication Data

US 2015/0094466 A1   Apr. 2, 2015

Related U.S. Application Data

(62) Division of application No. 13/749,594, filed on Jan. 24, 2013, now Pat. No. 8,877,921.

(60) Provisional application No. 61/590,741, filed on Jan. 25, 2012, provisional application No. 61/591,200, filed on Jan. 26, 2012.

(51) Int. Cl.
*C07D 453/06* (2006.01)
*C07D 487/22* (2006.01)
*C07D 471/22* (2006.01)

(52) U.S. Cl.
CPC ........... *C07D 487/22* (2013.01); *C07D 471/22* (2013.01)

(58) Field of Classification Search
CPC .................................................. C07D 453/06
USPC ........................................................ 540/579
See application file for complete search history.

(56) References Cited

U.S. PATENT DOCUMENTS

| | | |
|---|---|---|
| 2,813,873 A | 11/1957 | Janot et al. |
| 2,877,229 A | 3/1959 | Taylor |
| 3,516,989 A | 6/1970 | Sallay |
| 3,557,126 A | 1/1971 | Sallay |
| 3,574,220 A | 4/1971 | Sallay |
| 3,639,408 A | 2/1972 | Nagata et al. |
| 3,715,361 A | 2/1973 | Epstein et al. |
| 3,716,528 A | 2/1973 | Nagata et al. |
| 3,875,011 A | 4/1975 | Rubenstein et al. |
| 4,107,288 A | 8/1978 | Oppenheim et al. |
| 4,272,541 A | 6/1981 | Kotick et al. |
| 4,375,414 A | 3/1983 | Strahilevitz |
| 4,422,955 A | 12/1983 | Bryant |
| 4,444,758 A | 4/1984 | Scherschlicht et al. |
| 4,462,941 A | 7/1984 | Lee et al. |
| 4,464,378 A | 8/1984 | Hussain |
| 4,499,096 A | 2/1985 | Lotsof |
| 4,573,995 A | 3/1986 | Chen et al. |
| 4,587,243 A | 5/1986 | Lotsof |
| 4,604,365 A | 8/1986 | O'Neill et al. |
| 4,620,977 A | 11/1986 | Strahilevitz |
| 4,626,539 A | 12/1986 | Aungst et al. |
| 4,661,492 A | 4/1987 | Lewis et al. |
| 4,668,232 A | 5/1987 | Cordes et al. |
| 4,737,586 A | 4/1988 | Potier et al. |
| 4,806,341 A | 2/1989 | Chien et al. |
| 4,857,523 A | 8/1989 | Lotsof |
| 5,026,697 A | 6/1991 | Lotsof |
| 5,075,341 A | 12/1991 | Mendelson et al. |
| 5,145,684 A | 9/1992 | Liversidge et al. |
| 5,149,538 A | 9/1992 | Granger et al. |
| 5,152,994 A | 10/1992 | Lotsof |
| 5,283,247 A | 2/1994 | Dwivedi et al. |
| 5,290,784 A | 3/1994 | Qu et al. |
| 5,316,759 A | 5/1994 | Rose et al. |
| 5,382,657 A | 1/1995 | Karasiewicz et al. |
| 5,426,112 A | 6/1995 | Zagon et al. |
| 5,552,406 A | 9/1996 | Mendelson et al. |
| 5,574,052 A | 11/1996 | Rose et al. |
| 5,578,645 A | 11/1996 | Askanazi et al. |
| 5,580,876 A | 12/1996 | Crain et al. |
| 5,591,738 A | 1/1997 | Lotsof |
| 5,616,575 A | 4/1997 | Efange et al. |
| 5,618,555 A | 4/1997 | Tokuda et al. |
| 5,703,101 A | 12/1997 | Rose et al. |
| 5,726,190 A | 3/1998 | Rose et al. |
| 5,760,044 A | 6/1998 | Archer |
| 5,861,422 A | 1/1999 | Rose et al. |
| 5,865,444 A | 2/1999 | Kempf et al. |
| 5,925,634 A | 7/1999 | Olney |
| 5,935,975 A | 8/1999 | Rose et al. |
| 6,211,360 B1 | 4/2001 | Glick et al. |
| 6,291,675 B1 | 9/2001 | Coop et al. |
| 6,348,456 B1 | 2/2002 | Mash et al. |
| 6,451,806 B2 | 9/2002 | Farrar |

(Continued)

FOREIGN PATENT DOCUMENTS

| | | |
|---|---|---|
| CA | 2039197 | 9/1995 |
| DE | 22 17 132 | 10/1972 |

(Continued)

OTHER PUBLICATIONS

Buchli et al., "Chemical Transformations of Ibogaine," Journal of the American Chemical Society, 88:11, Jun. 5, 1966, pp. 2532-2535.
Extended European Search Report on EP Application 13740942.1, mailed Sep. 10, 2015.
JD Roberts, "Separation and Purification. Identification of Organic Compounds by Spectroscopic Techniques," Chapter 9, 1977 pp. 257-349.
Office Action on Chinese Application 201280058362.5, issued Aug. 5, 2015, English translation provided.
"Analysis—HPLC-Interchim technology", Interchim.com, pp. B31-B93, 2008.

(Continued)

*Primary Examiner* — Brenda Coleman
(74) *Attorney, Agent, or Firm* — Foley & Lardner LLP

(57) ABSTRACT

Synthetic voacangine, including in substantially enantiomerically enriched forms, and derivatives thereof are provided.

4 Claims, 6 Drawing Sheets

(56) References Cited

U.S. PATENT DOCUMENTS

| | | | |
|---|---|---|---|
| 6,806,291 | B1 | 10/2004 | Sunkel et al. |
| 6,864,271 | B2 | 3/2005 | Bazan et al. |
| 7,220,737 | B1 | 5/2007 | Mash |
| 7,737,169 | B2 | 6/2010 | Corrie et al. |
| 7,745,479 | B2 | 6/2010 | Nettekoven et al. |
| 7,754,710 | B2 | 7/2010 | Mash |
| 8,017,151 | B2 | 9/2011 | Batrakova et al. |
| 8,178,524 | B2 | 5/2012 | Mash |
| 8,362,007 | B1 | 1/2013 | Mash et al. |
| 8,637,648 | B1 | 1/2014 | Mash et al. |
| 8,741,891 | B1 | 6/2014 | Mash |
| 8,765,737 | B1 | 7/2014 | Mash et al. |
| 8,802,832 | B2 | 8/2014 | Mash et al. |
| 2003/0153552 | A1 | 8/2003 | Mash et al. |
| 2003/0158202 | A1 | 8/2003 | Caldirola et al. |
| 2006/0051317 | A1 | 3/2006 | Batrakova et al. |
| 2007/0185085 | A1 | 8/2007 | Mash |
| 2009/0264653 | A1 | 10/2009 | Bartolini et al. |
| 2010/0249105 | A1 | 9/2010 | Schrimpf et al. |
| 2010/0311722 | A1 | 12/2010 | Mash |
| 2010/0311723 | A1 | 12/2010 | Mash |
| 2010/0311724 | A1 | 12/2010 | Mash |
| 2010/0311725 | A1 | 12/2010 | Mash |
| 2012/0083485 | A1 | 4/2012 | Mash |
| 2012/0253037 | A1 | 10/2012 | Moriarty et al. |
| 2013/0072472 | A1 | 3/2013 | Gless et al. |
| 2013/0131046 | A1 | 5/2013 | Moriarty et al. |
| 2013/0165414 | A1 | 6/2013 | Gless et al. |
| 2013/0165647 | A1 | 6/2013 | Moriarty et al. |
| 2013/0303756 | A1 | 11/2013 | Mash et al. |
| 2014/0179684 | A1 | 6/2014 | Mash et al. |
| 2014/0179685 | A1 | 6/2014 | Mash et al. |
| 2014/0315837 | A1 | 10/2014 | Mash et al. |
| 2014/0315891 | A1 | 10/2014 | Mash |
| 2014/0357741 | A1 | 12/2014 | Mash et al. |

FOREIGN PATENT DOCUMENTS

| | | |
|---|---|---|
| EP | 2 338 494 | 6/2011 |
| GB | 0 841 697 | 7/1960 |
| GB | 0 924 042 | 4/1962 |
| GB | 1 256 914 | 12/1971 |
| GB | 1 378 348 | 12/1974 |
| GB | 2 271 059 | 4/1994 |
| JP | 04-221315 | 8/1992 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/03127 A1 | 2/1996 |
| WO | WO-99/11250 | 3/1999 |
| WO | WO-2007/012464 | 2/2007 |
| WO | WO-2007/070892 | 6/2007 |
| WO | WO-2012/012764 A1 | 1/2012 |
| WO | WO-2013/065850 | 5/2013 |
| WO | WO-2013/085850 | 6/2013 |
| WO | WO-2013/085922 A1 | 6/2013 |
| WO | WO-2013/148572 | 10/2013 |

OTHER PUBLICATIONS

Ahuja, Satinder (Ed.), "Chiral Separation Methods for Pharmaceutical and Biotechnological Products", John Wiley & Sons (published on line Oct. 2010).

Ala-Hurula, et al. "Erogotamine Abuse: Results of Ergotamine Discontinuation, with Special Reference to the Plasma Concentrations," Cephalalgia, 2:4 1982, abstract only.

Ala-Hurula, et al. "Tolfenamic Acid and Ergotamine Abuse," Headache, 21:6, 1981, abstract only.

Alexander. "A Procedure for Drug Screening Without the Need to Transport Urines Use of Ion Exchange Papers and Hem Agglutination." Clinical Toxicology, 9:3, 1976, abstract only.

Alim, et al. "Open-Label, Dose Run-Up Study of Diethylpropion in Initial Cocaine Abstinence," Clinical Neuropharmacology, 17:2, 1994, abstract only.

Almeida. "Use and Abuse of Alcohol and Drugs a Clinical Study of Certain Aspects of Their Interrelationship," Boletin de la Oficina Sanitaria Panamericana, 88:1, 1980, abstract only.

Al-Shabanah, et al. "Gastric Antiulcer and Cytoprotective Effects of Cathinone, a Psychoactive Alkaloid of Khat (Catha Edulis Forsk.) and Amphetamine in Rats," Regulatory Peptides, abstract only, 1994.

Altman et al., "An Improved Cu-Based Catalyst System for the Reactions of Alcohols with Aryl Halides," J. Org. Chem., (2008.), 73(1):284-286.

Azevedo, et al. "Adrenergic Nerve Degeneration Induced by Condensation Products of Adrenaline and Acetaldehyde," Naunyn-Schmiedeberg's Archives of Pharmacology, 300:2, 1977, abstract only.

Bagal, et al. "Modulation of Morphine-Induced Antinociception by Ibogaine and Noribogaine," Brain Research, 741:1-2, 1996, pp. 258-262.

Bartlett, et al. "The Alkaloids of Tabernanthe iboga. Part IV. The Structures of Ibogamine, Ibogaine, Tabernanthine and Voacangine." Journal of the American Chemical Society, 80, 1958, pp. 126-136.

Batrakova. "Pluronic P85 Enhances the Delivery of Digoxin to the Brain: In Vitro and In Vivo Studies", The Journal of Pharmacology and Experimental Therapy, 296, 2001, pp. 551-557.

Baumann et al. "Comparative Neurobiology of Ibogaine and its Metabolite, 12-Hydroxyibogaimine (Noribogaine), in Rodents," Conference at New York University, Abstract only, 1999.

Baumann et al., In vivo Neurobiological Effects of Ibogaine and Its o-Desmethyl Metabolite, 12 Hydroxyibogamine (Noribogaine), in Rats, J. Pharmacol. Exp. Ther. 2001, vol. 297, No. 2, pp. 531-539.

Beaubrun. "The Diagnosis and Management of Acute Psychotic Reaction Due to Alcohol and Drugs", Caribbean Medical Journal, 36:1, 1975, abstract only.

Beck, et al. "Energy-Dependent Reduced Drug Binding as a Mechanism of Vince Alkaloid Resistance in Human Leukemic Lymphoblasts", Molecular Pharmacology, 24:3, 1983, abstract only.

Beesley et al., "Chiral Chromatography", John Wiley & Sons (1998).

Benet, et al. "Pharmacokinetics: Biotransformation of Drugs." In Gilman et al. Goodman and Gilman's the Pharmacological Basis of Therapeutics, 1990, pp. 13-16.

Benoist, et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunology Immunotherapy, 30:5, 1989 abstract only.

Bert, et al. "Non-Amphetaminic Central Stimulation by Alkaloids from the Ibogaine and Vobasine Series", Planta Medicina, 54:3, 1988, abstract only.

Bhargava, et al. "Effects of ibogaine and noribogaine on the antinociceptive action of mu-, delta- and kappa-opioid receptor agonists in mice", Brain Research 752, 1997, pp. 234-238.

Bloomer et al., "Arc/Arg3.1 Translation Is controlled by Convergent N-Methyl-D-aspartate and Gs-coupled Receptor Signaling Pathways," J. Bio. Chem. (2008), 283(1):582-592.

Blum, et al. "Peyote a Potential Ethnopharmacologic Agent for Alcoholism and Other Drug Dependencies Possible Biochemical Rationale", Clinical Toxicology, 11:4, 1977, abstract only.

Blum, et al. "Possible Role of Tetrahydroisoquinoline Alkaloids in Postalcohol Intoxication States", Annals of the New York Academy of Science, 273, 1976, abstract only.

Blum, et al. "Putative Role of Isoquinoline Alkaloids in Alcoholism: A Link to Opiates", Alcoholism: Clinical and Experimental Research, 2:2, 1978, abstract only.

Brady, et al. "Analgesic Effects of Intraventricular Morphine and Enkephalins in Nondependent and Morphine-Dependent Rats," Journal of Pharmacology and Experimental Therapy, 222:1, 1982, abstract only.

Buchi, et al. "The total synthesis of iboga alkaloids," Jounal of the American Chemical Society, 88, 1966, pp. 3099-3109.

(56) References Cited

OTHER PUBLICATIONS

Bundgaard. "Design of Prodrugs: Bioreversible Derivatives for Various Functional Groups and Chemical Entities." Design of Prodrugs, 1-10, 1985.
Bussel, et al. "Isolated Thrombocytopenia in Patients Infected with HIV Treatment with Intravenous Gamma Globulin," American Journal of Hematology, 28:2, 1988, abstract only.
Caccamese et al., "Chiral HPLC Separation and CD Spectra of the Enantiomers of the Alkaloid Tacamonine and Related Compounds", Chirality (2001), 13:691-93.
Caldwell, et al. "The Biochemical Pharmacology of Abused Drugs. III. Cannabis, Opiates, and Synthetic Narcotics," Clinical Pharmacological Therapy, 16:6, 1974, abstract only.
CALPUS printout of Watts et al. "Alkaloids from Stemmadenia Species", I. Alkaloids of S. Donnellsmithiii and S. Galleottiana, (1958), vol. 2, pp. 173-182.
CALPUS printout of Zetler. "Some Pharmacological Properties of 12 Natural and 11 Partially Synthetic Indole Alkaloids from Tropical Apocyanaceae of the Subtribe Tabernaemontaninae", Arzneimittel-Forschung, (1964), 14:12, pp. 1277-1286.
Cankat. "Pharmacological Aspects of Drug Induced Headache", Functional Neurology, 7:6, 1992, abstract only.
Cappendijk, et al. "The Inhibitory Effect of Norharman on Morphine Withdrawal Syndrome in Rats: Comparison with Ibogaine." Behavioural Brain Research, 65, 1994, pp. 117-119.
Cappendijk, et al. "Inhibitory Effects of Ibogaine on Cocaine Self-Administration in Rats", European Journal of Pharmacology, 241:2-3, 1993, abstract only.
CAS Registry record for "Noribogaine" (1984).
Castle. "Drugs and Fibrotic Reactions—Part I", Adverse Drug React. Bull., 113: abstract only, 1985.
Chaturvedula et al, "New Cytotoxic Indole Alkaloids from Tabernaemontana calcarea from the Madagascar Rainforest", Journal of Natural Products, (2003), vol. 66, pp. 528-531.
Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.
Cherny, et al., Opioid responsiveness of cancer pain syndromes caused by neuropathic or nociceptive mechanisms: a combined analysis of controlled, single-dose studies, Neurobiology 44, 1994, pp. 857-861.
Cheze, et al. "Determination of ibogaine and noribogaine in biological fluids and hair by LC-MS/MS after Tabernanthe iboga abuse", Forensic Science International, Elsevierscientific Publishers Ireland Ltd, IE, vol. 176, No. 1, Nov. 19, 2007, pp. 58-66.
CN Office Action for CN Appl. No. 201180038173.7 dated Dec. 10, 2014.
Communication pursuant to Article 94(3) EPC for Appl. No. 11159572.4, dated Apr. 8, 2014.
Communication pursuant to Article 94(3) EPC for Appl. No. 11743404.3, dated Apr. 10, 2014.
Corey, E.J., "Catalytic Enantioselective Diels-Alder Reactions: Methods, Mechanistic Fundamentals, Pathways, and Applications," Angew. Chem. Int. Ed., (2002), 41:1650-1667.
Criel, et al. "Drug Dependent Red Cell Antibodies and Intravascular Haemolysis Occurring in Patients Treated with 9 Hydroxy-Methy;l-Ellipticinium," British Journal of Haematology, 46:4, 1980, abstract only.
Damstrup, et al. "Retroperitoneal Fibrosis After Long-Term Daily Use of Ergotamine," International Urology and Nephrology, 18:3, 1986, abstract only.

Database Registry (Online), Chemical Abstracts Service, Columbus Ohis, US Nov. 16, 1984, "ibogamine-18-carboxylic acid, 12-methoxy-,potassium sal," XP002638006, Database accession No. 5500-12-9.
Database Registry Chemical Abstracts Service, Columbus, Ohio, US; 1984. "Ibogamine-18-carboxylic acid, 12-methoxy-, potassium sal", Database accession No. 5500-12-9.
Deecher, et al. "Mechanisms of Action of Ibogaine and Harmaline Congeners Based on Radioligand Binding Studies." Brain Research 571, 1992, pp. 242-247.
Diener, et al. "Analgesic-Induced Chronic Headache Long-Term Results of Withdrawal Therapy," Journal of Neurology, 236:1, 1989, abstract only.
Dierckx, et al. "Intraarterial Sodium Nitroprusside Infusion in the Treatment of Severe Ergotism," Clinical Neuropharmacology, 9:6, 1986, abstract only.
Dzoljic, et al. "Effect of Ibogaine on Naloxone-Precipitated Withdrawal Syndrome in Chronic Morphine-Dependent Rats," Archives Internationales de Pharmacodynamie et de Thérapie, 294, 1988, pp. 64-70.
Eberwine, et al. "Molecular Analysis of Cellular Responses to Opiate Use", Fidia Research Foundation Symposium Series 7 (Neurotransmitter Regulation of Gene Transcription) 1991, abstract only.
Elkind. "Drug Abuse and Headache", Medical Clinics of North America, 75:3, 1991, abstract only.
EP Office Action, Communication Pursuant to Article 94(3) EPC dated Jun. 4, 2013 in related European Patent Application No. 11159572.4.
European extended search report for EP Appl. No. 12763567.0 dated Oct. 20, 2014.
European Office Action dated Apr. 17, 2015 in European Patent Application No. 11743404.
Evenson. "Developments in Therapeutic Drug Monitoring and Alkaloid Analysis", Federation Proceedings, 34:12, 1975, abstract only.
Extended European Search Report dated Jun. 6, 2011 in related European Patent Appl. No. 11159572.4.
Extended European Search Report issued on 12754746,5, mailed Apr. 23, 2015.
Faglia, et al. "Dihydroergocryptine in Management of Microprolactinomas," Journal of Clinical Endocrinology & Metabolism, 65:4, 1987 abstract only.
Fairchild, et al. "Keynote Address: Multidrug Resistance: A Pleiotropic Response to Cytotoxic Drugs," International Journal of Radiation, Oncology, Biology, & Physics, 20:2, 1991, abstract only.
Finkle. "Phencyclidine Identification by Thin-Layer Chromatography. A Rapid Screening Procedure for Emergency Toxicology", American Journal of Clinical Pathology, 70:2, 1978 abstract only.
First Examination Report for Australian Appl. No. 614366, dated Apr. 11, 2014.
First Office Action for Chinese Appl. No. 201180038173.7, dated Mar. 25, 2014.
Fonne-Pfister, et al. "Xenobiotic and Endobiotic Inhibitors of Cytochrome P-450dbl Function, the Target of the Debrisoquine / Sparteine Type Polymorphism," Biochemical Pharmacology, 37:20, 1988, abstract only.
Frances, et al. "Effects of Ibogaine on Naloxone-Precipitated Withdrawal in Morphine-Dependent Mice", Fundamental Clininical Pharmacology, 6:8-9, 1992, abstract only.
Futatsugi, et al., "Oxazaborolidine-Derived Lewis Acid Assited Lewis Acid as a Moisture-Tolerant Catalyst for Enantioselective Diels-Alder Reactions," Angew. Chem. Int. Ed., (2005), 44:1484-1487.
Gabr, et al. "Changes in Absolute Amount of Alkaloids in Datura-Metel Treated with Certain Growth Regulators", Herba Pol, 21:2, 1975, abstract only.
Garcia, et al. Chronic pain states: pathophysiology and medical therapy, Seminars in Arthritis and Rheumatism, 27, 1997, pp. 1-16.
Gennaro. "Remington: The Science and Practice of Pharmacy", Mack Publishing Col., vol. II, 1995, pp. 1736 & 1814.
George, et al. "Palliative medicine", Postgraduate Medical Journal, vol. 69, 1993, pp. 426-449.

(56) References Cited

OTHER PUBLICATIONS

Gifford, A. N. and Johnson, K. Gifford, et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41:4, 1992, abstract only.
Glick, et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657, 1994, pp. 14-22.
Glick, et al. "Effect of Ibogaine on Acute Signs of Morphine Withdrawal in Rats: Independence from Tremor", Neuropharmacology, 31:5, 1992, abstract only.
Glick, et al. "Effects of Aftereffects of Ibogaine on Morphine Self-Administration in Rats", European Journal of Pharmacology, 195:3, 1991, abstract only.
Glick, et al. "Ibogaine-like effects of noribogaine in rats", Brain Research, 713, 1996, pp. 294-297.
Glick, et al. "Local Effects of Ibogaine on Extracellular Levels of Dopamine and Its Metabolites in Nucleus Accumbens and Striatum: Interactions with D-Amphetamine", Brain Research, 628:1-2, 1993, abstract only.
Gold, et al. "Effect of Methadone Dosage on Clonidine Detoxification Efficacy", American Journal Psychiatry, 137:3, 1980, abstract only.
Gothoni. "Harmine-, Lon-954- and 5-Hydroxytryptophan-Induced Tremors in Rats Withdrawn from Ethanol", Acta Pharmacologica et Toxicologica, Copenhagen, DK, 57:1, 1985, abstract only.
Greenwald, et al., "Poly(ethylene glycol) conjugated drugs and prodrugs: a comprehensive review," Crit. Rev. Ther. Drug Carrier Syst., (2000), 17(2):101-161.
Gross. "Effect of Ergot Alkaloids on Serum Prolactin in Non-Psychotic Organic Brain Syndrome of the Elderly", Experimental Aging Research, 5:4, 1979, abstract only.
Gunn. "Relations Between Chemical Constitution, Pharmacological Actions, and Therapeutic Uses, in the Harmine Group of Alkaloids." From the Pharmacological Laboratory, University of Oxford, 1935, pp. 379-396.
Haber, et al. "Tetrahydroisoquinolines—Endogenous Products After Chronic Alcohol Abuse", Pharmazie, 47:1, 1992, abstract only.
Halikas, et al. "Treatment of Crack Cocaine Use with Carbamazepine", American Journal of Drug and Alcohol Abuse, 18:1, 1992, abstract only.
Hanks. "Opioid-responsive and opioid-non-responsive pain in cancer," British Medical Bulletin 47, 1991, pp. 718-731.
Hardman, et al. "Goodman & Gilman's The Pharmacological Basis of Therapeutics" (9th ed, 1996) p. 51 and pp. 57-58.
Harsing, et al. "Evidence that Ibogaine Releases Dopamine from the Cytoplasmic Pool in Isloated Mouse Striatum", Journal of Neural Transmission General Section, 96:3, 1994, abstract only.
Hearn, et al. "Identification and Quantitation of Ibogaine and an o-Demethylated Metabolite in Brain and Biological Fluids Using Gas Chromatography-Mass Spectrometry." Journal Analytical Toxicology, 19, 1995, pp. 427-434.
Heel, et al. "Buprenorphine: A Review of Its Pharmacological Properties and Therapeutic Efficacy", Drugs, 17:2, 1979, abstract only.
Henry, et al. "Reversible Cerebral Arteriopathy Associated with the Administration of Ergot Derivatives", Cephalalgia, 4:3, 1984, abstract only.
Ho, et al. "Metabolism of Harmaline in Rats." Biochemical Pharmacology vol. 20, 1971, pp. 1313-1319.
Hoes. "Clinical Criteria for the Selection of Anxiolytics", Tijdschrift voor Therapie Geneesmiddel en Onderzoek, 9:9, 1984, abstract only.
Holbrook. "Nicotine Addiction." in Isselbacher et al. (ed.), "Harrison's Principals of Internal Medicine" 13th Ed., McGraw-Hill Inc., 1994, 2433-2437.
Holzner, et al. "The Neuroleptic Sleeping Course in Chronic Headache", Therapiewoche, 35/36: 1985, abstract only.
Huang, et al. "Cytotoxicity and Sister Chromatid Exchanges Induced in Vitro by Six Anticancer Drugs Developed in the People's Republic of China", Journal of the National Cancer Institute, 71:4, 1983, abstract only.
Hubens, et al. "Chronic Intake of a Hydrogenated Ergot Alkaloid Causing Peripheral Vascular Ischemia—A Case Report", Journal of Vascular Surgery, 21:4, 1987, abstract only.
Huffman, et al. "A Formal Synthesis of (±)-Ibogamine," Journal of Organic Chemistry, vol. 50, 1985, pp. 1460-1464.
International Preliminary Report on Patentability for PCT/US2012/067799, dated Jun. 19, 2014.
International Preliminary Report on Patentability for PCT/US2012/071052, issued Jun. 23, 2015.
International Search Report and Written Opinion dated Mar. 11, 2013 in related PCT Patent Application No. PCT/US12/71052.
International Search Report and Written Opinion dated Oct. 31, 2012 in related PCT Application No. PCT/US2012/030405.
International Search Report and Written Opinion dated Oct. 4, 2012 in related PCT Application Serial No. PCT/US2012/022255.
International Search Report for PCT/US2011/045081 dated Oct. 4, 2011.
Isler. "Treatment of Headache", Schweizerische Medizinische Wochenschrift, 114:35, 1984, abstract only.
Jaffe. "Drug Addiction and Drug Abuse", Goodman and Gilman's The Pharmacological Basis of Therapeutics, 8th Ed., date unknown, pp. 520-523 & pp. 559-568, 2000.
Jaffe. "Psychopharmacology and Opiate Dependence," U.S. Public Health Services Publication, 1957-1967: pp. 1836.
James. "Linkers for solid phase organic synthesis," Tetrahedron, 55, 1999, pp. 4855-4946.
Jana et al., "Progress in the Synthesis of Iboga-alkaloids and their Congeners," Organic Preparation and Procedures International, (2011), 43:541-573.
Jana et al., "Total synthesis of ibogaine, epiibogaine and their analogues", Tetrahedron. 2012. vol. 68, pp. 7155-7165.
Jane, et al. "High-Performance Liquid Chromatographic Analysis of Basic Drugs on Silica Columns Using Non-Aqueous Ionic Eluents. II. Application of UV, Fluorescence and Electrochemical Oxidation detection", Journal of Chromatography, 323:2, 1985, abstract only.
Jansen, et al. "Ethnopharmacology of Kratom and the Mitragyna Alkaloids", Journal of Ethnopharmacology, 23:1, 1988, abstract only.
Janzen. "History of Use of Psychotropic Drugs in Central Africa," Psychotropes, 1/2: 1983, abstract only.
Jarraya, et al., "N-(Hydroxymethyl)ibogaine," Acta Cryst., (2008), E64-vol. 64(9):o1739.
Justins. "Management strategies for chronic pain," Annals of the Rheumatic Diseases, vol. 55, 1996, pp. 588-596.
Kagan, et al., "Catalytic Asymmetric Diels-Alder Reactions," Chem. Rev., (1992), 92:1007-1019.
Kalix. "Khat: A Plant with Amphetamine Effects," Journal of Substance Abuse Treatment, 5:3, 1988 abstract only.
Kalix. "Pharmacological Properties of the Stimulant Khat", Pharmacological Therapy, 48:3, 1990, abstract only.
Keefner. "A Gas Chromatography-Mass Spectrometry (GCMS) Method for Ibogaine", Society for Neuroscience Abstracts, 19:1-3, 1993, abstract only.
Keller, et al. "Modulation of Neopterin Release by Human Kupffer Cells in Culture: Possible Implication in Clinical Monitoring of HIV-Seropositive Subjects", Cells Hepatic Sinusoid, 3: 1991, abstract only.
Kingston et al., "Cytotoxicity of Modified Indole Alkaloids", Journal of Pharmaceutical Sciences, 68:11, Nov. 1979, pp. 1403-1405.
Knoll. "Azidomorphines and Homopyrimidazols: A New Approach to the Ideal Analgetic," ACTA Physiologica et Pharmacologica Bulgarica, 3:2, 1977, abstract only.
Knoll. "Azidomorphines: A New Family of Potent Analgesics with Low Dependence Capacity," Progress in Neuro-Psychopharmacology and Biological Psychiatry, 3:1-3, 1979, abstract only.
Koch, et al. "Drug-Induced Liver Injury in Liver Biopsies of the Years 1981 and 1983, their Prevalence and Type of Presentation", Pathology, Research and Practice, 179: 1985, abstract only.

(56) References Cited

OTHER PUBLICATIONS

Konig. "Psychiatric Intensive Therapy After Acute Alkaloid Withdrawal Syndrome", Infusionsther Klin Ernahr, 6:1, 1979, abstract only.

Kontrimaviciute et al., "Liquid chromatography-electrospray mass spectrometry determination of ibogaine and noribogaine in human plasma and whole blood: Application to a poisoning involving Tabernanthe iboga root" J. Chromatog. B (2006), 843, 131-41.

Kornetsky. "Pharmacology Drugs Affecting Behavior." John Wiley & Sons, 1976, pp. 185-187.

Kostowski, et al. "The Effects of Some Hallucinogens on Aggressiveness of Mice and Rats" Pharmacology, 7, 1972, pp. 259-263.

Krug. "Cocaine Abuse: Historical, Epidemiologic, and Clinical Perspectives for Pediatricians", Advances in Pediatrics, 36:369-406, 1989.

Kuehne et al., "Biomimetric syntheses of indole alkaloids. 11. Syntheses of .beta.-carboline and indoloazepine intermediates," J. Org. Chem., (1985), 50(7):919-924.

Kupers, et al. "Morphine differentially affects the sensory and affective pain ratings in neuorgenic and idiopathic forms of pain." Pain, 47, 1991, pp. 5-12.

Kuroch et al., "Voacanga Africana: Chemistry, Quality and Pharmacological Activity" ACS Symposium Series 1021 (African Natural Plant Products), (2009), 363-80.

Lakoski, et al. "Electrophysiologic Characterization of an Ibogaine Metabolite in Dorsal Raphe Nucleus and Hippocampus." Society for Neuroscience, 21:716, 1995, abstract only.

Larson-Prior, et al. "Electrophysiologic Characterization of an Ibogaine Metabolite in the Cerebellar Cortex." Society for Neuroscience, 21:716, 1995, abstract only.

Layer, et al., "Structurally modified ibogaine analogs exhibit differing affinities for NMDA receptors," European Journal of Pharmacology, 1996, 309:159-165.

Lemontt, et al. "Increase MDR Gene Expression and Decreased Drug Accumulation in Multidrug-Resistant Human Melanoma Cells", Cancer Research, 48:22, 1988, abstract only.

Leonard, J. "A Practical Introduction to Separation and Purification techniques for the Beginning Organic Chemistry Laboratory", Chem. Ed. (1981), 58, 1022-23.

Leoni, et al. "Effect of Cocaine and Morphine on Neutral Endopeptidase Activity of Human Peripheral Blood Mononuclear Cells Cultures with Lectins," Cell Biochemistry and Function, 11:3, 1993, abstract only.

Lerida, et al. "Incidence of Morphine Withdrawal and Quasi-Abstinence Syndrome in a Model of Chronic Pain in the Rat," Neuroscience, 81:1-2, 1987, abstract only.

Lewis, "Studies on the synthesis and biosynthesis of indole alkaloids", The Faculty of Graduate Studies Department of Chemistry University of British Columbia, (1978), See compound 220, Figure 57. abstract only.

Lewis, et al. "Adverse Reactions and Interactions with .beta.-Adrenoceptor Blocking Drugs," Journal of Medical Toxicology, 1:5, 1986, abstract only.

Lewis, et al. "Narcotic Analgesics and Antagonists," Annual Review of Pharmacology, 11, 1971, abstract only.

Licht, et al. "Induction of Multiple-Drug Resistance During Anti-Neoplastic Chemotherapy In-Vitro," International Journal of Cancer, 49:4, 1991, abstract only.

Ling, et al. "Drugs of Abuse-Opiates", in Addtiction Medicine [Special Issue], Western Journal of Medicine, 152, 1990, pp. 565-572.

Low, et al. "Effects of Acronycine and Cytouchalasin B on the Division of Rat Leukemia Cells," Experimental Cell Research, 131:1, 1981, abstract only.

Ma, et al. "Inhibition of Respiratory Burst Activity in Alveolar Macrophages by Bisbenzylisoquinoline Alkaloids: Characterization of Drug-Cell Interaction", Experimental Lung Research, 18:6, 1992, abstract only.

Maisonneuve, et al. "Interactions of Ibogaine and D-Amphetamine: in vivio Microdialysis and Motor Behavior in Rats." Brain Research 579, 1992, pp. 87-92.

Maisonneuve, et al. "Acute and Prolonged Effects of Ibogaine on Brain Dopamine Metabolism and Morphine-Induced Locomotor Activity in Rats", Brain Research, 575:1, 1992, abstract only.

Maisonneuve, et al. "Interactions Between Ibogaine, a Potential Anti-Addictive Agent, and Morphine: an in Vivo Microdialysis Study," European Journal of Pharmacology, 199:1, 1991, abstract only.

Martellotta, et al. "Effects of the Calcium Antagonist Isradipine on Cocaine Intravenous Self-Administration in Rats", Psychopharmacologia, 113:3-4, 1994, abstract only.

Martin, et al. "Neuropathic Pain in Cancer Patients: Mechanisms, Syndromes, and Clinical Controversies," Journal of Pain and Symptom Management, 14:2, 1997, pp. 99-117.

Mash, et al. "Ibogaine in the Treatment of Heroin Withdrawal," The Alkaloids 56, 2001, pp. 1-17.

Mash, et al. "Ligand Binding Profiles of Ibogaine and its O-demethylated Metabolite Noribogaine: Implications for Developing Novel Multi-target Anti-addiction Agents." Society of Neurosciences, vol. 21, 1995, abstract only.

Mash, et al. "Preclinical screening of an ibogaie metabolite (noribogaine) on cocaine-induced hyperlocomotion and cocaine self-administration." Society of Neurosciences, vol. 22, 1996, abstract only.

Mash, et al. "Properties of Ibogaine and its Principle Metabolite (12-hydroxyibogamine) at the MK-801 binding site of the NMKDA receptor complex," Neuroscience Letters, 192, 1995 pp. 53-56.

Mateer, et al. "Reversible Ipecac Myopathy," Archives of Neurology, 42:2, 1985, abstract only.

Matharu, et al. "Preformulation and Development of Ibogaine Injection for the Treatment of Drug Abuse," Pharmaceutical Research, 10: 1993, abstract only.

Mattingly, et al. "Selective Antagonism of Dopamine D Sub 1 and D Sub 2 Receptors Does Not Block the Development of Behavioral Sensitization to Cocaine," Psychopharmacologia, 114:2, 1994, abstract only.

McNeish, et al. "The 5-HT Sub 3 Antagonist Zacopride Attenuates Cocaine-Induced Increases in Extracellular Dopamine in Rat Nucleus Accumbens," Pharmacology, Biochemistry, and Behavior, 45:4, 1993, abstract only.

Melchior, et al. "Preference for Alcohol Evoked by Tetra Hydro Papaveroline Chronically Infused in the Cerebral Ventricle of the Rat," Pharmacol Biochem Behav, 7:1, 1977, abstract only.

Mendelson & Mello "Cocaine and Other Commonly Abused Drugs." In Isselbacher et al. (ed.), "Harrison's Principals of Internal Medicine." 13th Ed., McGraw-Hill Inc., 1994, pp. 2429-2433.

Menzies, et al. "Gangrene of the Small Bowel: A Complication of Methysergide Therapy," Australian and New Zealand Journal of Surgery, 52:5, 1982, abstract only.

Metelitsa. "Pharmacological Agents in Controlling Smoking," Biull Vsesoiuznogo Kardiol Nauchn Tsentra, 10:1, 1987, abstract only.

Millan. "k-Opioid Receptors and Analgesia," Trendes in Pharmacologicla Sciences, 11, 1990, pp. 70-76.

Mizuhashi, et al. "Antitumor Activities of IKP-104 a 4-1H Pyridizinone Derivative on Cultured and Implanted Tumors," Japanese Journal of Cancer Research, 81:12, 1990, abstract only.

Montefiori, et al. "In Vitro Evaluation of Mismatched Double-Stranded RNA (Ampligen) for Combination Therapy in the Treatment of Acquired Immunodeficiency Syndrome," AIDS Research and Human Retroviruses, 5:2, 1989 abstract only.

Mulamba, et al. "Alkaloids from Tabernathe Pubescens," Journal of Natural Products, vol. 44:2, 1981, pp. 184-189.

Naikwadi et al., "Liquid Chromatography of Phenolic Compounds on a Microbore Anion Exchange Resin Column," Analytical Chemistry, 56:8, 1984, p. 1525-1527.

Naranjo. "Ibogaine in psychotherapy: psychoanalysis according to Naranjo", part IV, pp. 1-2. http://www.nettuno.it/fiera/electric.italy/bwitif.html (1969).

Niemann et al, "The Isolation of Rupicoline and Montanine, Two Pseudoindoxyl Alkaloids of Tabernaemontana Rupicola Benth", The Journal of Organic Chemistry, 31(7):2265-2269, 1966.

(56) References Cited

OTHER PUBLICATIONS

Nishiyama, et al. "Expression of the Multidrug Transporter, P-Glycoproteiin, in Renal and Transitional Cell Carcinomas," Cancer, 71:11, 1993, pp. 3611-3619.

Nooter, et al. "Multidrug Resistance (MDR) Genes in Haematological Malignancies," Cytotechnology, 12:1-3, 1993, abstract only.

Nunn-Thompson, et al. "Pharmacotherapy for Making Cessation", Clin Pharm, 8:10, 1989, abstract only.

Obach, et al., "Cythochrome P4502D6 Catalyzes the O-Demethylation of the Psychoactive Alkaloid Ibogaine to 12-Hydroxyibogamine," Drug Metabolism and Disposition 26:8, 1998, pp. 764-768.

Office Action for Israeli Patent Application No. 227593 dated Nov. 13, 2013.

Office Action on Japanese Application 2013-520892, mailed Jul. 7, 2015.

O'Hearn, et al. "Degeneration of Prukinje Cells in Parasagittal Zones of the Cerebellar Vermis After Treatment with Ibogaine of Harmaline," Neuroscience, 55:2, 1993, abstract only.

O'Hearn, et al. "Ibogaine Induces Glial Activation in Parasagittal Zones of the Cerebellum," Neuroreport, 4:3, 1993, abstract only.

Pablo, et al, "Noribogaine Stimulates Naloxone-Sensitive[35S]GTPgammaS Binding," NeuroReport, 9, 1998, pp. 109-114. (Website Publication Date of Dec. 20, 1997.).

Pacifici, et al. "Immunological Effect of Cocaine and Host Resistance in Mice," International Journal of Immunotherapy, 8:2, 1992, abstract only.

Palyi. "Survivial Responses to New Cytostatic Hexitols of P388 Mouse and K562 Leukemia Cells in Vitro," Cancer Treatment Reports, 70:2, 1986, abstract only.

Pantazis, et al. "Efficacy of Camptothecin Congeners in the Treatment of Human Breast Carcinoma Xenografts," Oncology Research, 5:8, 1994, abstract only.

PCT International Preliminary Report on Patentability dated Jul. 30, 2013 in related PCT International Patent Application No. PCT/US2012/022255.

PCT International Preliminary Report on Patentability for PCT/US2012/067629 dated Nov. 13, 2014.

PCT International Search Report and Written Opinion dated Dec. 8, 2014 for PCT Application No. PCT/US2014/031364.

PCT International Search Report and Written Opinion dated Jan. 21, 2015 in PCT Patent Application No. PCT/US2014/034826.

PCT International Search Report and Written Opinion for related PCT/US2013/022874, dated Jun. 28, 2013.

PCT International Search Report and Written Opinion in related PCT Patent Application No. PCT/US12/67799, dated Mar. 28, 2013.

PCT International Search Report in PCT/US2012/067629 dated Mar. 13, 2013.

Pehek. "Effects of Cathinone and Amphetamine on the Neurochemistry of Dopamine in Vivo," Neuropharmacology, 29:12, 1990, abstract only.

Percheron et al., Ibogaine et vocangine. Compt. Rend. Acad. Sci., (1957), 245:1141-1143.

Perera, et al. "Tertiary Indole Alkaloids of Tabernaemontana Dichotoma Seeds," Planta Medica, 49:1, 1983, abstract only.

Perrin. "Clinical Pharmacokinetics of Ergotamine in Migraine and Cluster Headache," Clinical Pharmacokinetics, 10:4, 1985, abstract only.

Popik, et al. "NMDA Antagonist Properties of the pUtative Antiaddictive Drug, Ibogaine," Journal of Pharmaceutical and Experimental Therapeutics, 275:2, 1995, pp. 753-760.

Popik, et al. "The Putative Anti-Addictive Drug Ibogaine is a Competitive Inhibitor of (SUP 3 H) Binding to the NMDA Receptor Complex", Psychopharmacologia, 114:4, 1994, abstract only.

Popik, et al. "100 Years of Ibogaine: Neurochemical and Pharmacological Actions of a Putative anti-addictive Drug," Pharmacological Reviews 47:2, 1995, pp. 235-253.

Pulvirenti, et al. "Lisuride Reduces Intravenous Cocaine Self-Administration in Rats," Pharmacology, Biochemistry and Behavior, 47:4, 1994, abstract only.

Qiu, et al. "The Influence of Chronic Nicotine Treatment on Stress-Induces Gastric Ulceration and Emptying Rate in Rats," Experientia, 48:4, 1992, abstract only.

Radouco-Thomas, et al. "Adverse effects to Psychotomimetics. Proposition of a Psychopharmacological Classification." Pharmacologie, Toxicologie, et abus des psychotomimetiques (hallucinogens), (1974), 109, abstract only.

Rezvani, et al. "Noribogaine, a Primary Ibogaine Metabolite, Reduces Alcohol Intake in P and Fawn-Hooded Rats." RSA Annual Scientific Meeting, 1995, abstract only.

Rezvani, et al. "Reduction of Alcohol Intake in Alcohol Preferring Fawn-hooded and P Rats by Noribogaine, the Primary Metabolite of Ibogaine." NIDA Monograph Series 162:281, 1996, Abstract only.

Ricceri, et al. "Postnatal cocaine Esposure Affects Neonatal Passive Avoidance Performance and Cholinergic Development in Rats," Pharmacology, Biochemistry and Behavior, 45:2, 1993, abstract only.

Rodriguez, et al. "Cocaine Adminstration Prior to Reactivation Facilitates Later Acquisition of an Avoidance Response in Rats," Psychopharmacologia, 112:2-3, 1993, abstract only.

Rosenmund, et al. "Ibogamin, Ibogain and Epiibogamin" Chemische Berichte, 108, 1975, pp. 1871-1895.

Sachs, et al. "Corneal Complications Associated with the Use of Crack Cocaine," Ophthalmology, 100:2, 1993, abstract only.

Salmoiraghi, et al. "Effects of LSD 25, BOL 148, Bufotenine, Mescaline and Ibogaine on the Potentiation of Hexobarbital Hypnosis Produced by Serotonin and Reserpine." Journal of Pharmacology and Experimental Therapeutics 120:1, 1957, pp. 20-25.

Samadi-Baboli, et al. "Preparation of Low Density Lipoprotein-9-Methoxy-Illipticin Complex and Its Cytotoxic Effect Against L1210 and P 388 Leukemic Cells in Vitro," European Journal of Cancer and Clinical Oncology , 25:2, 1989, abstract only.

Saper, et al. "Ergotamine Tartrate Dependency: Features and Possible Mechanisms," Clinical Neuropharmacology, 9:3, 1986, abstract only.

Schecter, et al. "Comparison of the Behavioral Effects of Ibogaine from Three Sources: Mediation of Discriminative Activity," European Journal of Pharmacology, 249:1, 1993, abstract only.

Schneider, et al. "Analysis of the Cardiovascular Action of Ibogaine Hydrochloride." Archives Internationales de Pharmacodynamie et de Thérapie, 110, 1957, pp. 92-102.

Schneider, et al. "Neuropharmacological Studies of Ibogaine: An Indole Alkaloid with Central Stimulant Properties." Annals of the New York Academy of Sciences, 66, 1957, pp. 765-776.

Schneider, et al., "Potentiation Action of Ibogaine on Morphine Analgesia" Experiential, 12, 1956, pp. 323-324.

Schnider, et al. "Use and Abuse of Analgesics in Tension-Type Headache," Cephalalgia, 14:2, 1994, abstract only.

Schuckit & Segal. "Opiod Drug Use." In Isselbacher et al. (ed.), "Harrison's Principals of Internal Medicine" 13th Ed., McGraw-Hill Inc., 1994, 2425-2429.

Schuckit. "Alcohol and Alcoholism," In Isselbacher et al. (ed.), "Harrison's Principals of Internal Medicine." 13th Ed., McGraw-Hill Inc., 1994, pp. 2420-2425.

Seeber, et al. "In Vivo Resistance Towards Anthracyclines, Etoposide, and Cis-Diamminedichloroplatinum (II)," Cancer Research, 42:11, 1982, abstract only.

Sehested, et al. "The Carboxylic Ionophore Monensin Inhibits Active Drug Efflux and Modulates In-Vitro Resistance in Daunorubicin Resistant Enrlich Ascites Tumor Cells," Biochemical Pharmacology, 37:17, 1988 abstract only.

Sershen, et al. "Ibogaine Antagonizes Cocaine-Induced Locomotor Stimulation in Mice," Life Sciences, 50:15, 1992, abstract only.

Sershen, et al. "Ibogaine Reduces Amphetamine-Induced Locomotor Stimulation in C57BL/6By Mice, but Stimulates Locomotor Activity in Rats," Life Sciences, 51:13, 1992, abstract only.

Sershen, et al. "Ibogaine Reduces Preference for Cocaine Consumption in C57BL/6By Mice," Pharmacology Biochemistry and Behavior, 47:1, 1994, abstract only.

Shen, et al. "Antagonists at Excitatory Opioid Receptors on Sensory Neurons in Culture Increase Potency and Specificity of Opiate Analgesics and Attenuate Development of Tolerance/ Dependence," Brain Research, 636:2, 1994, abstract only.

(56) References Cited

OTHER PUBLICATIONS

Sheppard. "A Preliminary Investigation of Ibogaine: Case Reports and Recommendations for Further Study." Journal of Substance Abuse Treatment, 11:4, 1994, abstract only.
Shir, et al. "Neuropathic pain unrelieved by morphine, alleviated by haloperidol," Harefuah 118:8, 1990, abstract only.
Shook et al. "A cyclic Somatostatin Analog that Precipitates Withdrawal in Morphine-Dependent Mice", NIDA Res. Monogr., 76(Probl. Drug Depend.): abstract only, 1987.
Sinkula, et al. "Rationale for Design for Biologically Reversible Drug Derivatives: Prodrugs." Journal of Pharmaceutical Sciences, 64:2, 1975, pp. 181-210.
Sjostromt et al., "Ion Exchange Separation Method for Microdetermination of Tropane Alkaloids in the Presence of Mkphine," 1959, XP55182014.
Slotkin, et al. "A Model of Harmine Metabolism in the Rat." The Journal of Pharmacology and Experimental Therapeutics, 174:3, 1970, pp. 456-462.
Slotkin, et al. "Blood Levels and Urinary Excretion of Harmine and its Metabolites in Man and Rats." The Journal of Pharmacology and Experimental Therapeutics, 173:1, 1970, pp. 26-30.
Slotkin, et al. "Urinary Metabolites of Harmine in the Rat and their Inhibition of Monoamine Oxidase." Biochemical Pharmacology, 19, 1970, pp. 125-131.
Sloviter, et al. "A Common Mechanism of Lysergic Acid, Indolealkylamine and Phenethylamine Hallucinogens: Serotonergic Mediation of Behavioral Effects in Rats." Journal of Pharmacological Experimental Therapy, 214:2, 1980, pp. 231-238.
Smith. "Interaction of Biogenic Amines with Ethanol," Advances in Experimental Medicine and Biology, 56, 1975, abstract only.
Snyder, et al., "Practical HPLC Method Development", 1997, 2nd Ed., pp. 214-218, 266, 267, 282 & 283, John Wiley & Sons, Inc.
Solinas, et al. "Solid-Supported Reagents and Catch-and-Release Techniques in Organic Synthesis", Synthesis 2007:16, 2007, pp. 2409-2453.
Stahl, et al., "Handbook of Pharmaceutical Salts", 1998, p. 250 John Wiley & Sons.
Stella. "Pro-drugs as Novel Drug Delivery Systems", ed. Higuchi, T. et al., American Chemical Society, Washington D.C., 1975, pp. 1-49.
Stella. "Pro-drugs: An Overview and Definition." Prodrugs as Novel Drug Delivery System. ACS Symposium Series: 1975, pp. 1-115.
Stevenson et al, (Ed.), "Chiral Separations", Plenum Press (1987).
Still, et al., "Rapid Chromatorgraphic Technique for Preparative Separations with Moderate Resolutions", J. Org. Chem., (1978), 43, 2923-25.
Sugiyama, et al. "Quantitative Analysis of Cell-Kill Effects of Anticancer Drugs: Consideration of Both In Vitro and In Vivo Expreimental Systems." Gan to Kagaku Ryoho, 14:12, 1987, abstract only.
Suvarna et al., "Hydrolysis of N-Methyl-D-aspartate Receptor-Stimulated cAMP and cGMP by PDE4 and PDE2 Phosphodiesterases in Primary Neuronal Cultures of Rat Cerebral Cortex and Hippocampus," J. Pharmacol. Exp. Ther., (2002), 302(1):249-256.
Tarnower, et al., "Ergotism Masquerading as Arteritis," Postgradate Medicine, 85:1, 1989, abstract only.
Teoh, et al. "Buprenorphine Effects on Morphine- and Cocaine-Induced Subjective Responses by Drug-Dependent Men," Journal of Clinical Psychopharmacology, 14:1, 1994, abstract only.
Tfelt-Hansen, et al. "Nitroglycerin for Ergotism. Experimental Studies in Vitro and in Migraine Patients and Treatment of an Overt Case," European Journal of Clinical Pharmacology, 22:2, 1982, abstract only.
Third Office Action on Chinese Application 201180038173.7, issued Jun. 17, 2015—English translation provided.
Toda, Fumio (Ed.), "Enantiomer Separation: Fundamentals and Practical Methods", Kluwer Academic Publishers (2004).
Torrenegra, et al. "Alkaloids of stemmadenia grandiflora", Phytochemistry, 27:6, 1988, pp. 1843-1848.

Toyo'oka, "Resolution of chiral drugs by liquid chromatography based upon diastereomer formation with chiral derivatization reagents", J. Biochem. Biophys. Methods 54, 25-56 (2002).
Trost, et al., "A Total Synthesis of Racemic and Optically Active Ibogamine. Utilization and Mechanism of a New Silver Ion Assisted Palladium Catalyzed Cyclization," J. Am. Chem. Soc., (1978), 100(12):3930-3931.
Trost, et al., "Stereocontrolled Approach to 1,4-Disubstitued 1,3-Dienes," J. Org. Chem., (1978), 43(24):4559-4564.
Tsuruo. "Multidrug Resistance: A Transport System of Antitumor Agents and Xenobiotics," Princess Takamatsu Symp, 21, 1990, abstract only.
Uldry, et al. "Cerebrovascular Accidents in Relation to Drug Consumption or Drug Abuse," Schweizerische Rundschau Fur Medizin Praxis, 78:23, 1989, abstract only.
Valadez, et al. "Persistence of the Ability of Amphetamine Preexposure to Facilitate Acquistion of Cocaine Self-Administration," Pharmacology, Biochemistry and Behavior, 47:1, 1994, abstract only.
Valencia, et al. "Obovatine, a New Bisindole Alkaloid from Stemmadenia Obovata," Journal of Natural Products, 58:1, 1995, pp. 134-137.
Vescovi, et al. "Successful Treatment of Opiate Withdrawal Using Lysine Acetylsalicylate," Current Therapeutic Research, Clinical and Experimental, 33:5, 1983, abstract only.
Villalba, et al. "Uses and Abuses of Ipecacuana Syrup", Farmacia Clinica, 9:1, 1992, abstract only.
Wells, et al. "Recognition and Treatment of Arterial Insufficiency from Cafergot," Journal of Vascular Surgury, 4:1, 1986, abstract only.
Whitaker, et al. "High Affinity 3H-Serotonin Binding to Caudate: Inhibition by Hallucinogenic and Serotonergic Drugs," Psychopharmacology 59, 1978, pp. 1-5.
Whitaker, et al. "Selective Labeling of Serotonin Receptors by d'(3H)Lysergic Acid Diethylamide in Calf Caudate." Proceedings of the National Academy of Sciences 75:12, 1978, pp. 5783-5787.
Whittaker, et al. "Recurrent Laryngeal Nerve Paralysis in Patients Receiving Vincristine and Vinblastine", British Medical Journal, 1:6071, 1977, abstract only.
Widler, et al. "Pharmacodynamics and Pharmacokinetics of Khat: a Controlled Study," Clinical Pharmacology Therapy, 55:5, 1994, abstract only.
Wildmann. "Heterocycles as Physiological Ligands for the Benzodiazepine Receptor and for Other Binding Sites", Pharmacology Residency, 21:6, 1989, abstract only.
Williams, et al. "The 'Alice in Wonderland' Experience Ergot Alkaloid Therapy for Prolactin-Secreting Pituitary Tumors," The Western Journal of Medicine, 138:3, 1983, abstract only.
Wishart, et al. "Is Multidrug Resistance Relevant in Breast Cancer," European Journal of Surgical Oncology, 17:5, 1991, abstract only.
Witt, et al. "Pharmacodynamic and Pharmacokinetic Characterization of Poly(Ethylene glycol) Conjugation to Met-Enkephalin Analog [D-Pen2,D-Pen5]-enkephalin (DPDPE)", Journal of Pharmcological and Experimental Therapy, 298:2, 2001, pp. 848-856.
Witt, et al. "Pluronic P85 Block Copolymer Enhances Opioid Pepetide Analgesia," Journal of Pharmcology and Experimental Therapy, 303:2, 2002, pp. 760-767.
Worz. "Effects and Risks of Psychotropic and Analgesic Combinations," American Journal of Medicine, 75:5A, 1983, abstract only.
Yang, et al., "Prodrug based optimal drug delivery via membrane transporter/receptor," Expert. Opin. Biol. Ther., (2001), 1(2):159-175.
Zetler, et al. "Pharmacokinetics in the Rat of the Hallucinogenic Alkaloids Harmine and Harmaline." Naunyn-Schmiedeberg's Archives of Pharmacology, 285, 1974, pp. 273-292.
Zetler, et al. "Cerebral Pharmacokinetics of Tremor-Producing Harmala and Iboga Alkaloids" Pharmacology, 7:4, 1972, pp. 237-248.
Notification of Defects in Application issued on Israeli Application 232724, mailed Nov. 4, 2015.
Office Action issued on Russian Application 2013139382, mailed Dec. 4, 2015, English translation provided.

(56) References Cited

OTHER PUBLICATIONS

Vutukuri et al., "A Mild Deprotection Strategy for Allyl-Protecting Groups and Its Implications in Sequence Specific Dendrimer Synthesis," J.Org. Chem, vol. 68, 2003, pp. 1146-1149.
Communication issued on EP 11743404.3, mailed Nov. 16, 2015.
Glick SD et al., Development of novel medications for drugs addiction. The legacy od an African shrub. AnnN.Y.Acad.Sci. 2000; 909:808-103 abstract[on-line] [found on Aug. 21, 2015]www.ncbi.nlm.nih.gov/pubmed/10911925.
International Search Report & Written Opinion for PCT/US2014/013063 dated Oct. 8, 2015.
Office Action on Russian Application 2013102923/15 dated Aug. 11, 2015 English translation provided.
Peterson, A. L. et al., Treatment of Parkinson's disease with trophic factors. Neurotherapeutics, 2008, vol. 5, No. 2, pp. 270-280.
RN:5500-12-9,Registry (STN) [online] , Nov. 16, 1984.
RN:766444-34-2,Registry (STN) [online], Oct. 20, 2004.
Wang et al., Targeted Delivery of GDNF through the Blood-Brain Barrier by MRI-Guided Focused Ultrasound, PLoS One, vol. 7, Issue 12, Article e52925, internal pp. 1-8, Dec. 2012.
Examination Report issued on Australian Application 2012209332, mailed Feb. 10, 2016.
Office Action issued on Chinese Application 201180038173.7, mailed Jan. 8, 2016, English translation provided.
Office Action on Chinese Application 201110083808.7, mailed Jul. 15, 2015 English translation provided.
Russian Office Action on Application 2013102923/15 dated May 8, 2015, English translation included.
Second Office Action issued on Chinese Application 201280058362.5, mailed Feb. 22, 2016 English translation included.
Bandarage et al., Total Syntheses of Racemic Albifloranine and Its Anti-Addictive Congeners, Including 18- Methoxycoronaridine, Tetrahedron, vol. 55, No. 31, pp. 9405-9424 (1999).
CAS Printout of Passarella et al., Nature-Inspired Indolyl-2-Azabicyclo[2.2.2]oct-7-ene Derivatives as Promising Agents for the Attenuation of Withdrawal Symptoms:Synthesis of 20-Desethyl-20-Hydroxymethyl-11-Demethoxyibogaine, Natural Product Research, vol. 20, No. 8, pp. 758-765 (2006).
Huffman et al., The Synthesis of Desethylibogamine, Journal of the American Chemical Society, vol. 87, No. 10, p. 2288 (1965).

SYNTHETIC VOACANGINE

CROSS REFERENCE TO RELATED APPLICATION

This application is a divisional application and claims priority to U.S. patent application Ser. No. 13/749,594 filed on Jan. 24, 2013, which claims the benefit under 35 U.S.C. 119(e) of U.S. Provisional Application Ser. Nos. 61/590,741 filed Jan. 25, 2012, and 61/591,200 filed Jan. 26, 2012, each of which is hereby incorporated by reference into this application in its entirety.

FIELD OF THE INVENTION

This invention relates to processes for preparing synthetic voacangine, and salts thereof, intermediates thereto, and to compositions comprising the same.

STATE OF THE ART

Voacangine is an alkaloid found in plants such as *Tabernanthe Iboga* and *Voacanga Africana*, and has the following structure:

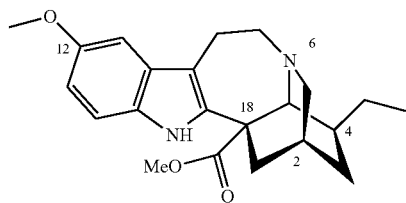 [SMILES: CC[C@H]1C[C@@H]2CN3CCc4c([nH]c5ccc(OC)cc45)[C@](C(=O)OC)(C2)C13]

It is an iboga alkaloid which can serve as a precursor for the semi-synthesis of ibogaine:

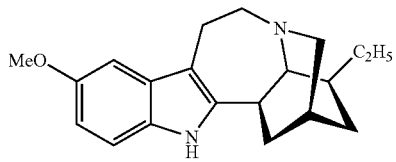

which can be demethylated to provide noribogaine:

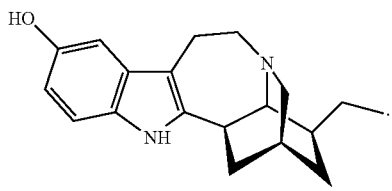 [SMILES: CC[C@H]1C[C@H]2C[C@H]3c4[nH]c5ccc(O)cc5c4CCN(C2)C13]

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737). Voacangine is a potential source for making noribogaine. However, plant derived voacangine is problematic because of its limited and unpredictable supply. Furthermore, plant derived voacangine may contain unwanted alkaloids which may find their way to the noribogaine produced from the plant derived voacangine.

Accordingly, there is an ongoing need to provide synthetic voacangine, which can be intermediates in the synthesis noribogaine, preferably in an enantiomerically enriched form.

SUMMARY OF THE INVENTION

This invention provides synthetic voacangine. In one embodiment, this invention provides (+) voacangine, (+) ibogaine, or (+) noribogaine, in a substantially enantiomerically enriched form. In some embodiments, the voacangine, ibogaine, or noribogaine provided herein contains less than 1 ppt, preferably less than 0.9 ppt $C^{14}$, more preferably, less than 0.75 ppt, and still more preferably, less than 0.2 ppt. In some embodiments, the voacangine is present as a racemic or scalemic mixture. As used herein, a "scalemic mixture" is a mixture of enantiomers at a ratio other than 1:1. In some embodiments, the voacangine is present in a substantially enantiomerically enriched form.

Also provided here are methods for producing synthetic voacangine and derivatives thereof, including in racemic, or in substantially enantiomerically enriched form. In particular, such derivatives include substitution at the 12 and/or 18 position of voacangine. When substitution is solely at the 12 position, such substitution is other than a methoxy group In some embodiment, the synthetic voacangine are obtained in a substantially enantiomerically enriched form.

DETAILED DESCRIPTION OF THE INVENTION

Figure 1A:
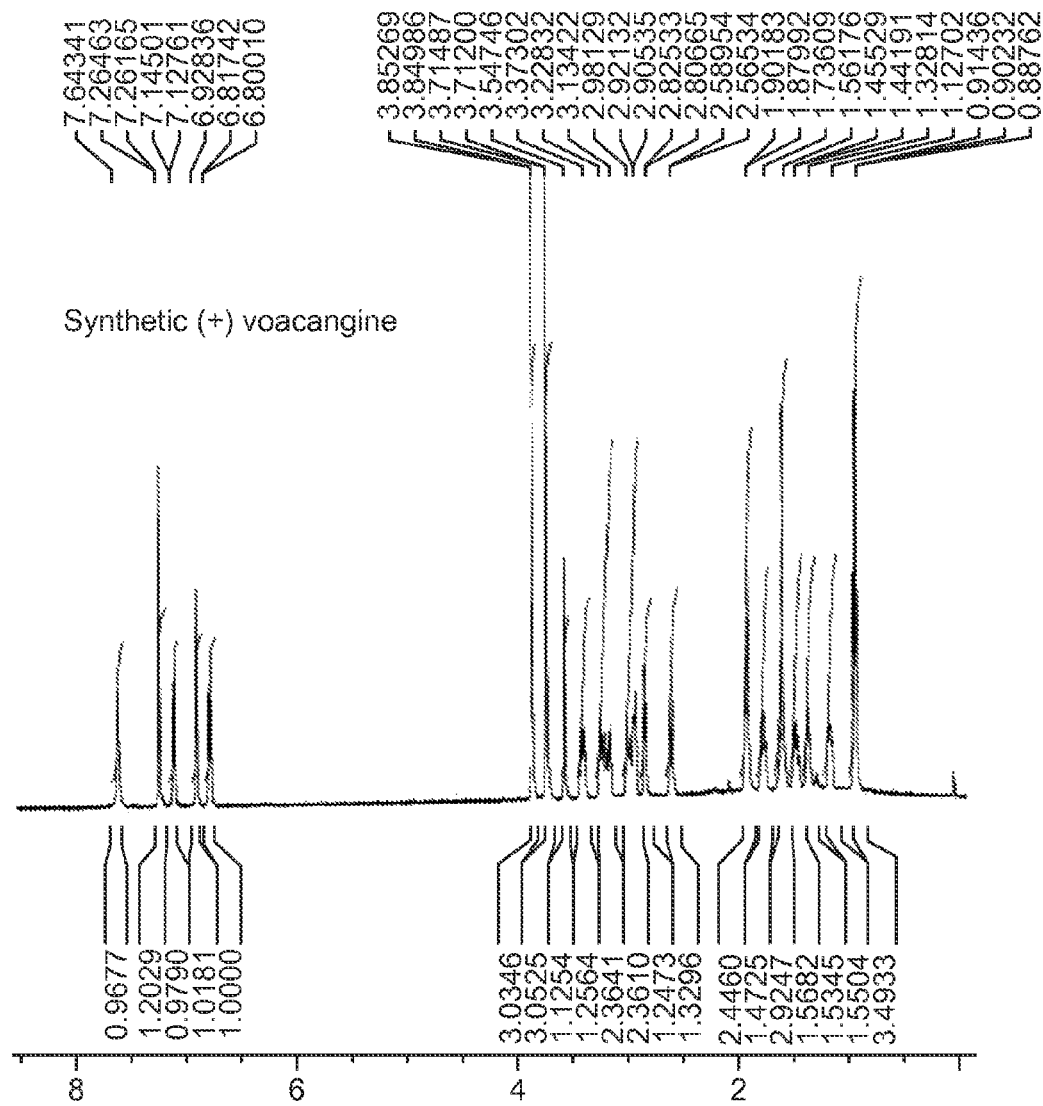
FIGS. 1A, 1B, and 1C illustrate $^1$H-NMR spectra in CDCl$_3$ of synthetic (+) voacangine, synthetic (+) ibogaine, and synthetic (+) noribogaine prepared according to this invention.

This invention is directed to synthetic voacangine, and substantially enantiomerically enriched forms thereof. However, prior to describing this invention in greater detail, the following terms will first be defined.

It is to be understood that this invention is not limited to particular embodiments described. It is also to be understood that the terminology used herein is for the purpose of describing particular embodiments only, and is not intended to be limiting, since the scope of this invention will be limited only by the appended claims.

It must be noted that as used herein and in the appended claims, the singular forms "a", "an", and "the" include plural referents unless the context clearly dictates otherwise. Thus, for example, reference to "a solvent" includes a plurality of such solvents.

Definitions

Unless defined otherwise, all technical and scientific terms used herein have the same meaning as commonly understood by one of ordinary skill in the art to which this invention belongs. As used herein the following terms have the following meanings.

As used herein, "(−)" enantiomer refers to the levorotatory enantiomer, and "(+)" enantiomer refers to the dextrorotatory enantiomer.

As used herein, "alkenyl" refers to hydrocarbyl groups having from 2 to 10 carbon atoms and at least one and up to 3 carbon carbon double bonds. Examples of alkenyl include vinyl, allyl, dimethyl allyl, and the like.

As used herein, the term "alkyl" refers to hydrocarbon groups having from 1 to 20, 1 to 6, or 1 to 3 carbon atoms. The alkyl group may contain linear or branched carbon chains. This term is exemplified by groups such as methyl, ethyl, n-propyl, iso-propyl, n-butyl, t-butyl, n-pentyl and the like.

As used herein, the term "alkoxy" refers to —O-alkyl.

As used herein, "alkynyl" refers to hydrocarbyl groups having from 2 to 10 carbon atoms and at least one and up to 2 carbon carbon triple bonds. Examples of alkynyl include ethynyl, propargyl, dimethylpropargyl, and the like.

As used herein, "amino" refers to —$NR^xR^y$ wherein each $R^x$ and $R^y$ independently is hydrogen, $C_1$-$C_6$ alkyl, $C_2$-$C_6$ alkenyl, $C_2$-$C_6$ alkynyl, or $R^x$ and $R^y$ together with the nitrogen atom they are bonded to form a 5-10 membered heterocyclyl ring containing 1-2 nitrogen and/or oxygen atoms, which heterocyclyl ring is optionally substituted with 1-3, preferably, 1-2, or more preferably, a single, $C_1$-$C_3$ alkyl group.

As used herein, the term "aryl" refers to an aromatic hydrocarbon ring having preferably 6 ring carbon atoms such as phenyl. "Substituted aryl" refers to aryl substituted with 1-3 $C_1$-$C_6$ alkoxy or $C_1$-$C_6$ alkyl groups.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, "$C_x$," refers to a group having x carbon atoms, wherein x is an integer, for example, $C_4$ alkyl refers to an alkyl group having 4 carbon atoms.

As used herein, "ee" refers to enantiomeric excess and is expressed as ($e^1$-$e^2$) % where $e^1$ and $e^2$ are the two enantiomers. For example, if the % of $e^1$ is 95 and the % of $e^2$ is 5, then the $e^1$ enantiomer is present in an ee of 90%. The ee of an enantiomer in a mixture of enantiomers is determined following various methods well known to the skilled artisan, such as using chiral lanthanide based nuclear magnetic resonance shift reagents, forming derivatives with chiral compounds such as chiral hydroxyacids, amino acids, and the like. Various physical measurements such as circular dichroism, optical rotation, etc. are also useful is determining the ee of a mixture of enantiomers.

As used herein, "heterocyclyl" or heterocycle refers to a cycloalkyl group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—), provided that the ring has at least 3 and up to 14, or preferably from 5-10 ring atoms. Such heterocyclyl groups can have a single ring or multiple condensed rings wherein the condensed rings may not contain a heteroatom and/or may contain an aryl or a heteroaryl moiety, provided that the point of attachment is through an atom of the non-aromatic heterocyclyl group. Examples of heterocyclyl include pyrrolidinyl, piperadinyl, piperazinyl, and the like. Heterocyclyl rings are preferably saturated, though, heterocyclyl rings including 1-2 carbon carbon double bonds are also contemplated provided that the ring is not aromatic.

As used herein, the term "protecting group" or "Pg" refers to well known functional groups which, when bound to a functional group, render the resulting protected functional group inert to the reaction to be conducted on other portions of the compound and the corresponding reaction condition, and which, at the appropriate time, can be reacted to regenerate the original functionality under deprotection conditions. The identity of the protecting group is not critical and is selected to be compatible with the remainder of the molecule. In one embodiment, the protecting group is an "amino protecting group" which protects the amino functionality of voacangine intermediates during the voacangine synthesis described herein. Examples of amino protecting groups include, for instance, benzyl, acetyl, oxyacetyl, carbonyloxybenzyl (Cbz), and the like. In another embodiment, the protecting group is a "hydroxy protecting group" which protects the hydroxyl functionality of voacangine intermediates during the voacangine synthesis described herein. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, and benzyl. Additional examples of amino and hydroxy protecting groups may be found in standard reference works such as Greene and Wuts, Protective Groups in Organic Synthesis, 2d Ed., 1991, John Wiley & Sons, and McOmie Protective Groups in Organic Chemistry, 1975, Plenum Press. Methods for protecting and deprotecting the phenolic hydroxyl group of the compounds disclosed herein can be found in the art, and specifically in Greene and Wuts, supra, and the references cited therein.

As used herein, the term "reaction conditions" refers to details under which a chemical reaction proceeds. Examples of reaction conditions include, but are not limited to, one or more of following: reaction temperature, solvent, pH, pressure, reaction time, mole ratio of reactants, the presence of a base or acid, or catalyst, etc.

As used herein, the term "salt" refers to salts derived from a variety of organic and inorganic counter ions well known in the art and include, by way of example only, when the molecule contains an acidic functionality, counter ions such as lithium, sodium, potassium, calcium, magnesium, ammonium, tetraalkyl ammonium, and the like, and when the molecule contains a basic functionality, counter ions such as acetate, citrate, chloride, bromide, lactate, mesylate, maleate, oxalate, phosphate, succinate, sulfonate such as methane sulfonate or para toluenedulfonate, tartrate and the like.

As used herein, "substantially enantiomerically enriched" refers to an enantiomer in an enantiomeric mixture with at least 90% ee, preferably 95% ee, or more preferably 98% ee.

As used herein, the term "voacangine" refers to the compound of formula:

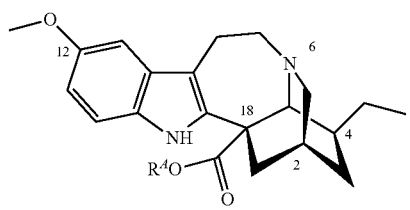

and salts thereof wherein $R^4$ is $C_1$-$C_6$ alkyl optionally substituted with 1-3 aryl groups, or $R^4$ is H, and includes all stereoisomers at the 2, 4, 6, and 18 position, and salts of each thereof. Of particular interest are compounds wherein $R^4$ is $C_1$-$C_4$ alkyl, and of more particular interest is the compound wherein $R^4$ is methyl.

Compounds and Compositions

This invention provides synthetic voacangine compositions which are enantiomerically enriched.

In one aspect, this invention provides synthetic voacangine and voacangine derivative compounds of formula:

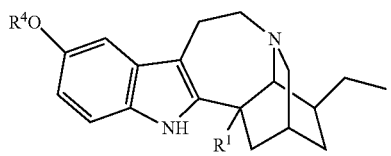

or salts thereof wherein, $R^1$ is —$COOR^2$, —$CH_2$—OH, or —$CH_2$—OC(=O)$R^3$;

$R^2$ is a metal cation, a $C_1$-$C_6$ alkyl optionally substituted with 1-3 phenyls or substituted phenyls, or with a hydroxy, —$NHCOCH_3$, or an amino group, where the substituted phenyl is substituted with 1-3, $C_1$-$C_6$ alkyl and/or $C_1$-$C_6$ alkoxy group, or $R^2$ is hydrogen;

$R^3$ is an asymmetric hydrocarbyl group such that $R^3COOH$ is a chiral carboxylic acid;

$R^4$ is $C_1$-$C_6$ alkyl, $C_1$-$C_6$ alkyl substituted with 1-3, halo, $C_1$-$C_6$ alkoxy, phenyl, or substituted phenyl, where the substituted phenyl is substituted with 1-3, $C_1$-$C_6$ alkyl and/or $C_1$-$C_6$ alkoxy group, or $R^4$ is another hydroxyl protecting group.

In a particular embodiment, $R^1$ is a carboxylate salt that is —COO$^-$Li$^+$ which is a stable, recoverable salt of the corresponding carboxylic acid.

In another embodiment, $R^2$ is $C_1$-$C_4$ alkyl. In a preferred embodiment, $R^2$ is methyl. In another embodiment, $R^2$ is $C_1$-$C_6$ alkyl substituted with 1-3 phenyls or substituted phenyls, where the substituted phenyl is substituted with 1-3, $C_1$-$C_6$ alkyl and/or $C_1$-$C_6$ alkoxy group.

In another embodiment, $R^1$ is —$CH_2$—OH. In another embodiment, $R^1$ is —$CH_2$—OOCR$^3$.

In certain embodiments, the synthetic compounds provided by this invention are provided in substantially enantiomerically enriched or diastereomerically enriched form.

Compounds wherein $R^1$ is —$COOR^2$ can be converted to noribogaine via treatment with aqueous hydrazine, and compounds wherein $R^1$ is —$CH_2$—OH can be converted to noribogaine under retro aldol condensation conditions, which reaction conditions will be apparent to the skilled artisan in view of this disclosure.

Certain preferred compounds of this invention are of formula:

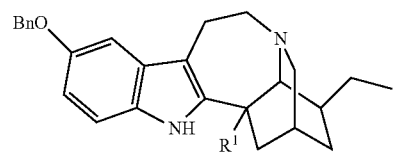

wherein $R^1$ is $CO_2(CH_2)_2OH$, $CO_2(CH_2)_2NHCOCH_3$, $CO_2(CH_2)_2NMe_2$,

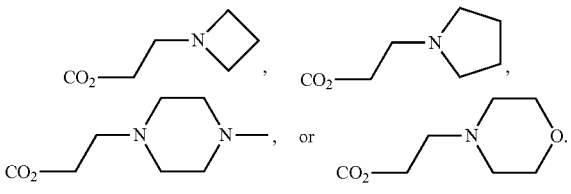

The synthetic voacangine, its substantially enantiomerically enriched forms, and other synthetic compounds of this invention are distinguished from such plant derived compounds (e.g., and without limitation, voacangine isolated from plant sources) by its $^{14}C$ content. $^{14}C$ has a half-life of about 5,730 years and is generated in the upper atmosphere as $^{14}CO_2$. The amount of $^{14}CO_2$ present is approximately 1 ppt (parts per trillion) and, through photosynthesis, accumulates in plants resulting in a $^{14}C$ content of plant material of approximately 1 ppt. Accordingly, plant derived voacangine is expected to have approximately 1 ppt $^{14}C$. Conversely, the synthetic compounds disclosed herein are derived from fossil fuels, which, due to $^{14}C$ decay, would have a $^{14}C$ content of less than 1 ppt $^{14}C$. Accordingly, provided herein is synthetic voacangine, ibogaine or noribogaine, preferably in the (+) form, or a voacangine derivative having a $^{14}C$ content of less than 1 ppt, preferably, less than 0.95 ppt, or more preferably less than 0.8 ppt. In one embodiment, provided herein is synthetic voacangine or a voacangine derivative having a $^{14}C$ content of less than 0.6 ppt, or less than 0.5 ppt, or less than 0.4 ppt, or less than 0.3 ppt, or less than 0.2 ppt, or less than 0.1 ppt. In another embodiment, provided herein is synthetic voacangine or a voacangine derivative having a $^{14}C$ content of 0.8 ppt to 0.95 ppt or 0.7 ppt to 0.95 ppt. The amount of $^{14}C$ can be analyzed using methods well known in the art (i.e. radiocarbon analyses can be carried out according to the American Society for Testing Materials ASTM D6866 procedure (ASTM international, 100 Barr Harbon Drive, PO Box C700, West Conshohocken, Pa. 19428-2959)). Furthermore, provided is a method for distinguishing synthetic voacangine or a voacangine derivative from plant derived voacangine or voacangine derivatives based on their respective $^{14}C$ content.

Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1 15 (John Wiley and Sons, 1991), Rodd's Chemistry of Carbon Compounds, Volumes 1 5 and Supplementals (Elsevier Science Publishers, 1989), Organic Reactions, Volumes 1 40 (John Wiley and Sons, 1991), March's Advanced Organic Chemistry, (John Wiley and Sons, 4th Edition), and Larock's Comprehensive Organic Transformations (VCH Publishers Inc., 1989).

Synthetic voacangine and 12-substituted derivatives thereof can be prepared as shown in the non limiting illustration below. For illustrative purposes only, the following discussion will illustrate reactions where $R^4$ is methyl.

Scheme 1

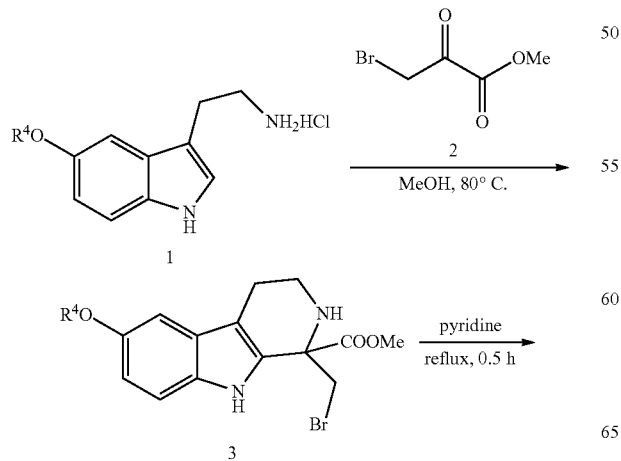

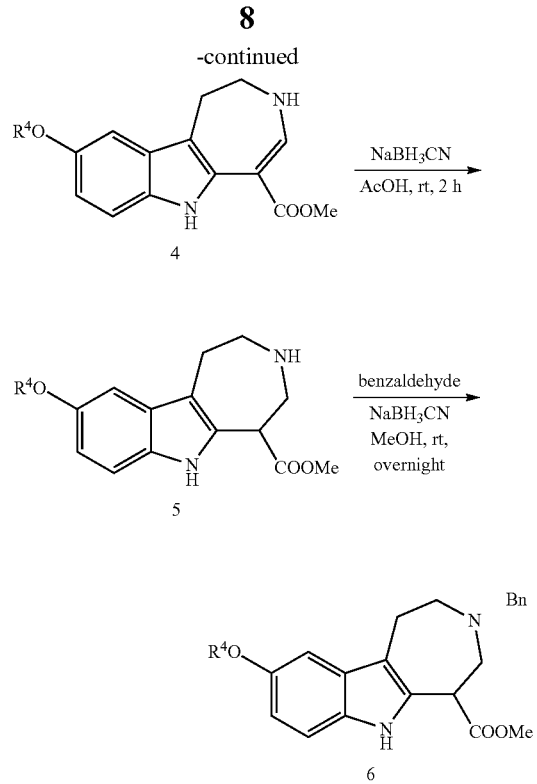

Scheme 2

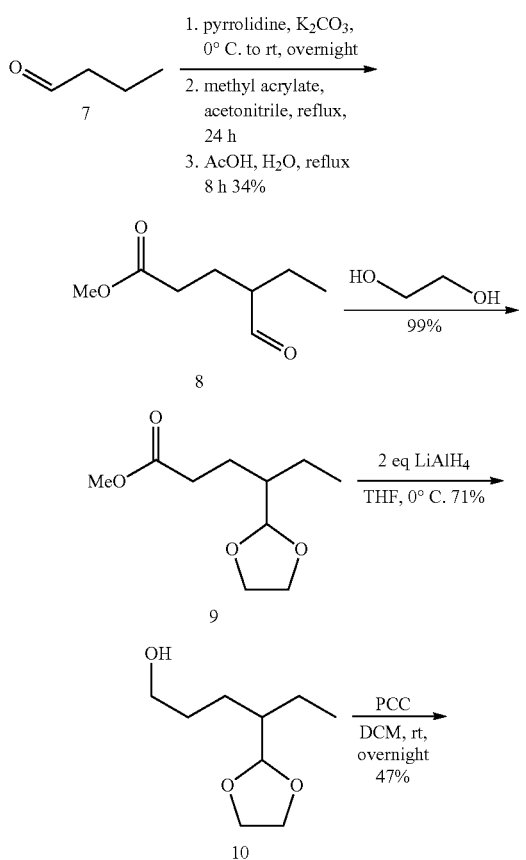

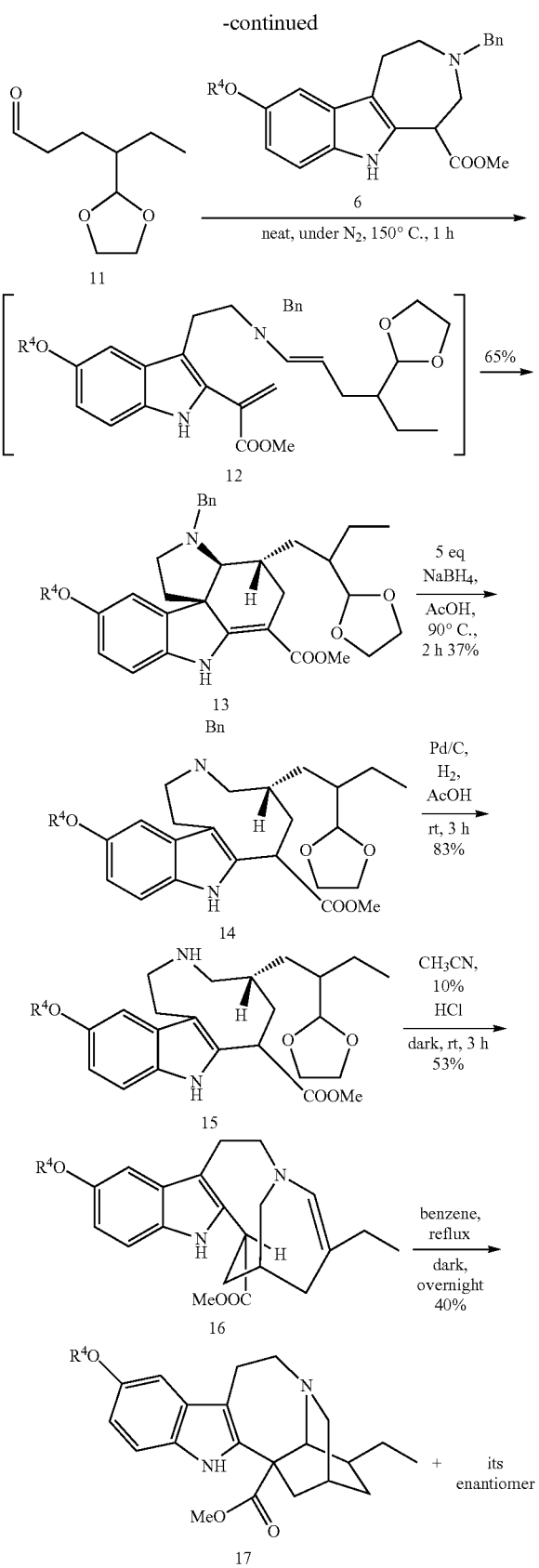

substituted phenyl is substituted with 1-3, $C_1$-$C_6$ alkyl and/or $C_1$-$C_6$ alkoxy group, or $R^4$ is another hydroxyl protecting group.

Compounds wherein $R^1$ is $COOR^2$ other than COOMe are synthesized by employing the corresponding $COOR^2$ group or by converting a compound such as Compound 17 to the corresponding $COOR^2$ ester, such as by refluxing with the corresponding $R^2OH$, as will be apparent to the skilled artisan.

According to the schemes above, compound 1 (200 g) was converted to compound 3 (120 g) by contacting compound 1 with compound 2 in an inert solvent such as methanol at an elevated temperature such as 80° C. The reaction product was recovered by conventional methods to provide for compound 3 in 43% yield. Compound 3 (130 g, 90% pure) was converted to compound 4 (60 g, 90% pure) by contacting compound 3 with pyridine at an elevated temperature, e.g., at a temperature where the pyridine refluxes, preferably for about 0.5 h. Without further separation, compound 4 (60 g), was converted to compound 5 (30 g, 90% pure) by contacting compound 4 with $NABH_3CN$ in acetic acid (AcOH) at room temperature, preferably for about 2 hours. Without further separation, compound 5 (30 g) obtained in the previous step was converted to compound 6 (15 g, 90% pure) by contacting compound 5 with benzaldehyde and $NABH_3CN$ in an inert solvent such as methanol at room temperature. Compound 6 was separated by column chromatography to yield compound 6 (15 g, 90% pure). Compound 7 was converted to compound 11 following a number of steps well known to the skilled artisan and described e.g., in Kuehne et al., J. Org. Chem., 50:919 (1985), incorporated herein in its entirety by reference. In the schemes above, the benzyl (Bn) protecting group can be replaced with other amino protecting groups well known to the skilled artisan.

As shown above, compound 6 was converted to compound 13 (30 g, 90% pure after column chromatographic separation) by contacting compound 6 with of compound 11, preferably under an inert $N_2$ atmosphere. Without further purification, Compound 13 (30 g) was contacted with of $NaBH_4$ and mL of AcOH at elevated temperature, such as 90° C., preferably for about 2 hours to yield compound 14 (20 g) after column chromatographic separation. Compound 14 (12 g) was deprotected by contacting with palladium/carbon and hydrogen in AcOH to yield compound 15 (10 g, 80% pure) in 90% purity. Compound 15 was contacted in darkness with of 10% HCl in an inert solvent such as acetonitrile, preferably for about 3 h to provide compound 16 (5 g) in 70% purity.

Figure 1B:
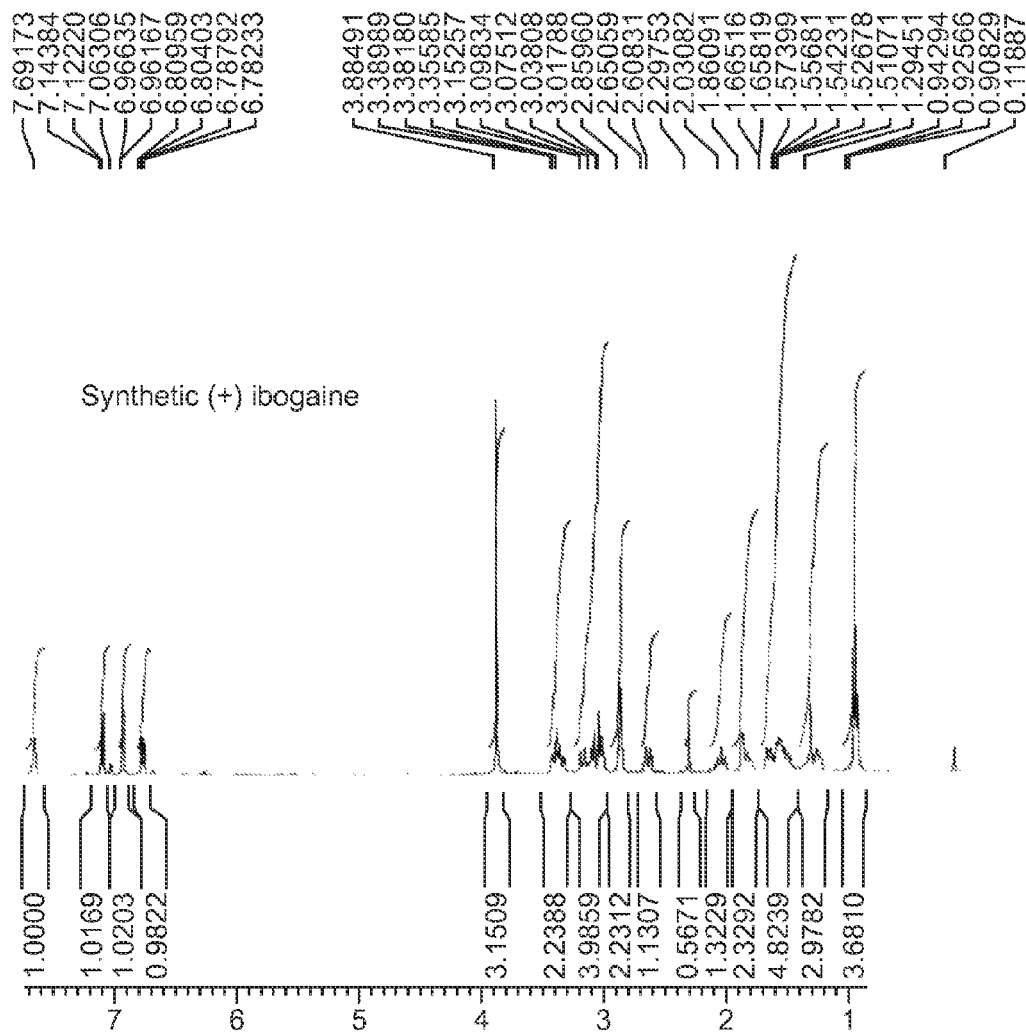
Figure 1C:
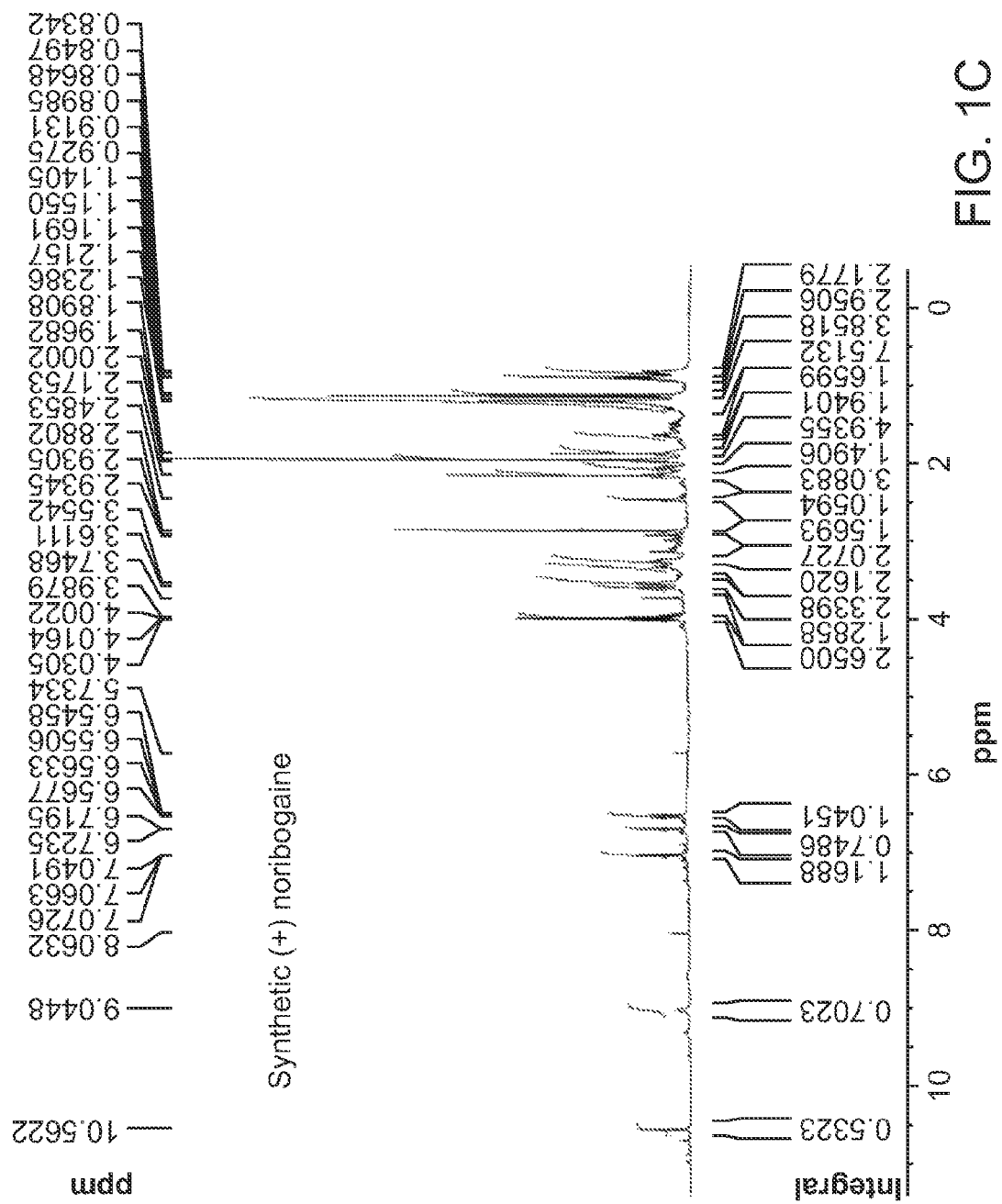
Figure 2A:
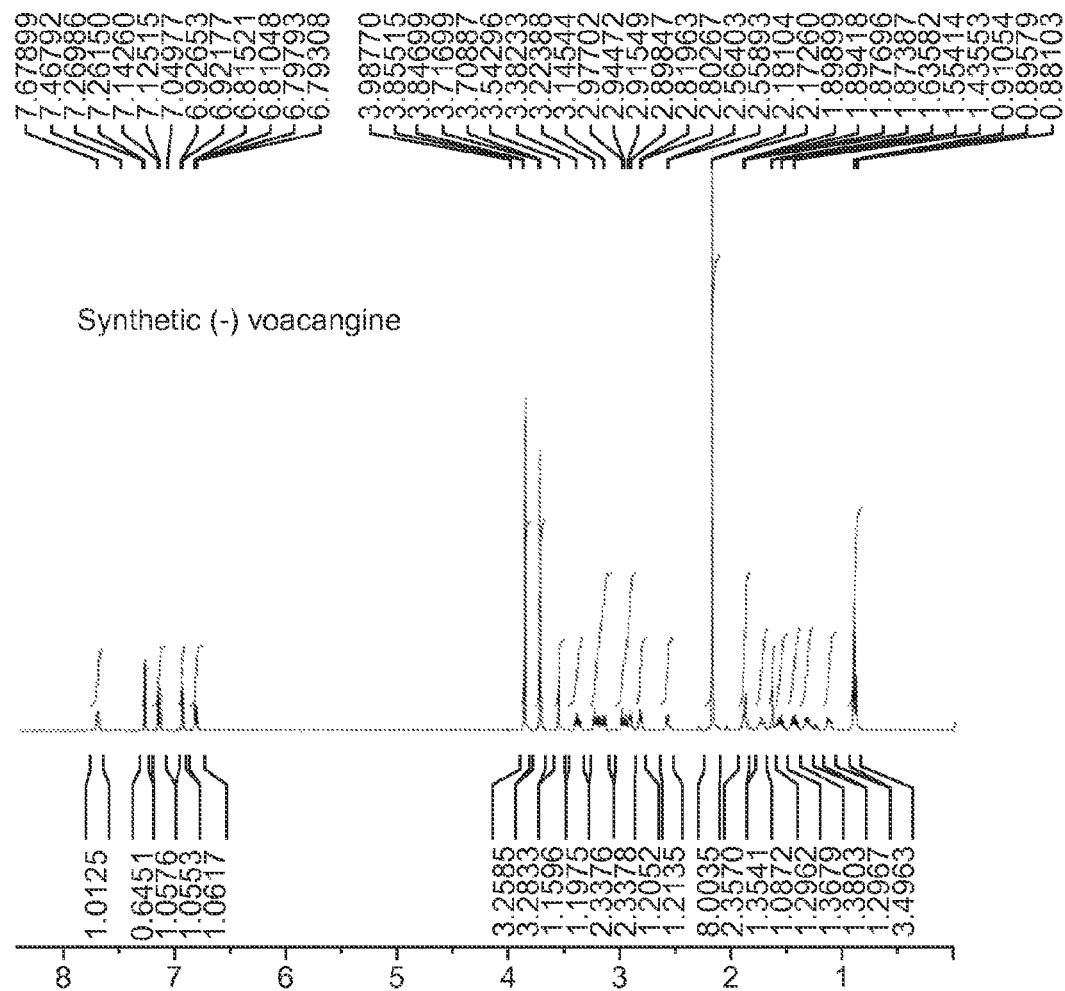
FIGS. 2A, 2B, and 2C illustrate $^1$H-NMR spectra in CDCl$_3$ of synthetic (−) voacangine, synthetic (−) ibogaine, and synthetic (−) noribogaine prepared according to this invention.
Figure 2B:
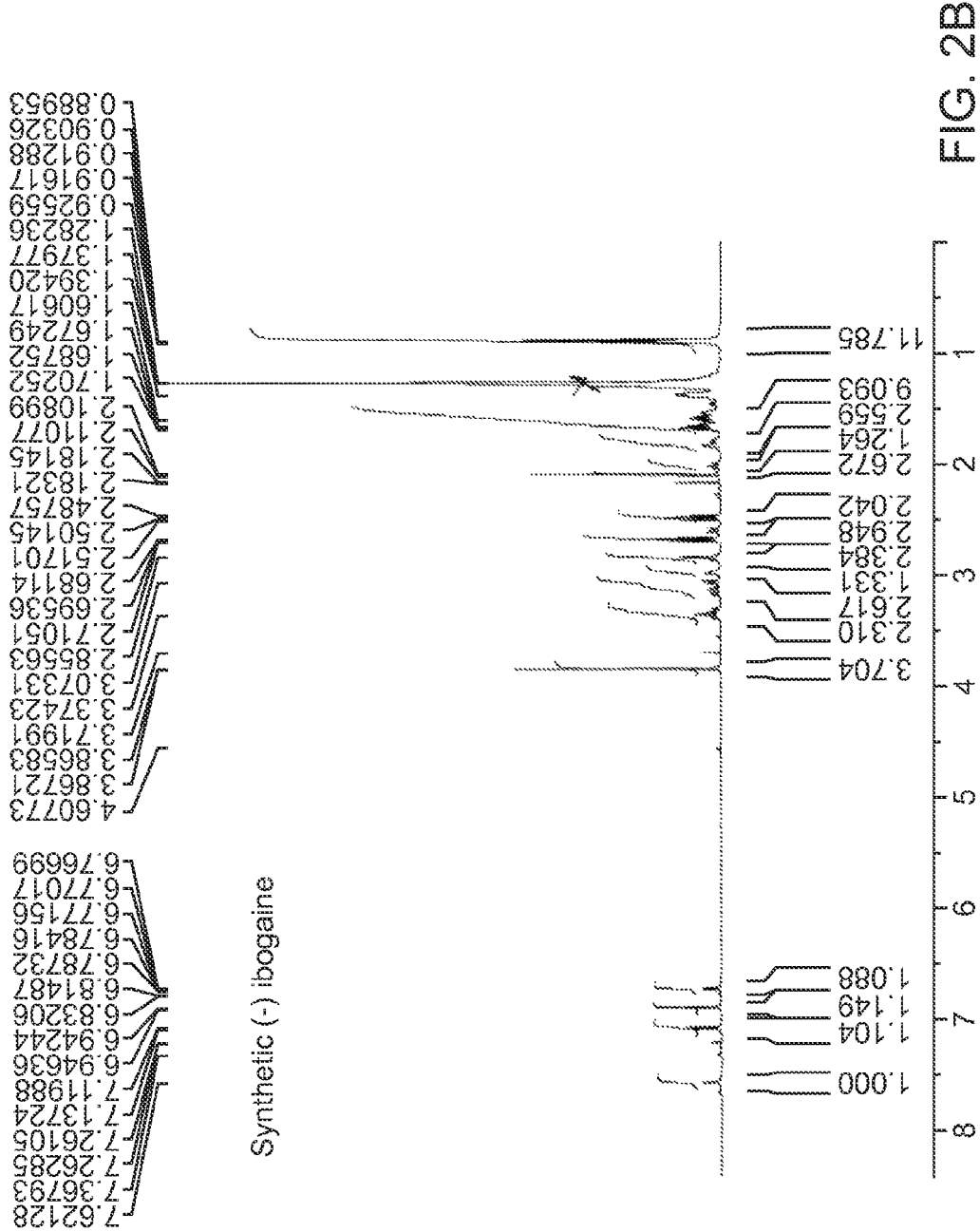
Figure 2C:
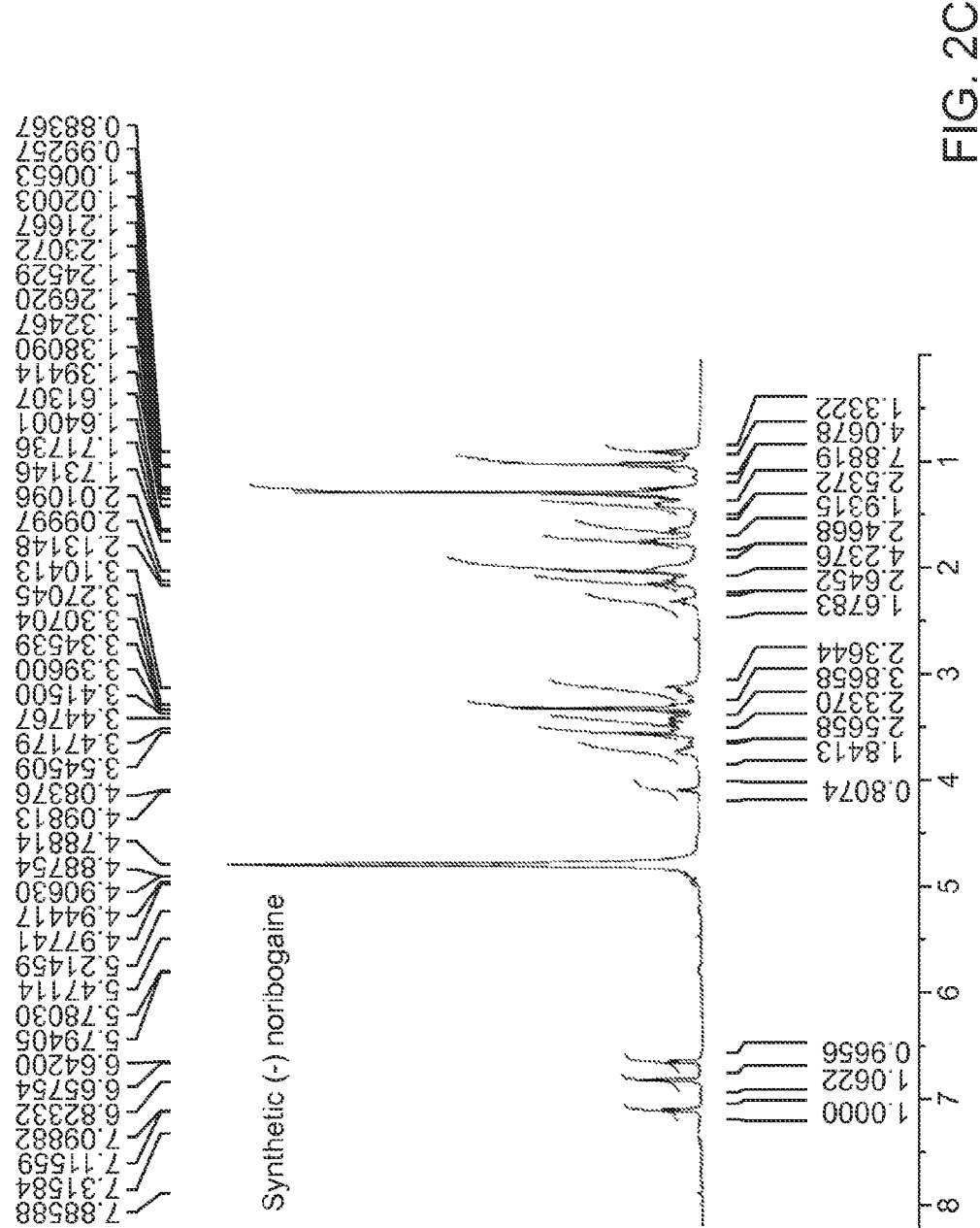

Compound 16 (0.5 g) was converted, without further purification, under cyclization conditions to racemic synthetic voacangine, compound 17 (2 g, 98% pure). Under the cyclization conditions, compound 16 was refluxed in darkness, in an inert solvent such as benzene for about 10 h. Throughout the synthesis, purity of the product was determined by high performance liquid chromatography optionally with mass spectrometry. The $^{13}C$ nuclear magnetic resonance (NMR) spectra and $^1H$ NMR spectra of the synthetic compound 17, where R4 is methyl (see, FIG. 1) and a standard sample demonstrated that synthetic compound 17 was indeed voacangine. For each of the steps, the contacting is continued until the reaction substantially complete, as determined by a variety of methods well known to the skilled artisan, such as thin layer chromatography and $^1H$-NMR. Certain preferred contacting times are provided herein. Compound 17 was separated by chiral supercritical fluid chromatography into 1 g each of the enantiomers, the where $R^4$ is $C_1$-$C_6$ alkyl, $C_1$-$C_6$ alkyl substituted with 1-3, halo, $C_1$-$C_6$ alkoxy, phenyl, or substituted phenyl, where the naturally occurring (−) voacangine and the non-natural (+) voacangine enantiomer, in substantially enantiomerically enriched form.

In one aspect, this invention provides a process for preparing a compound of formula:

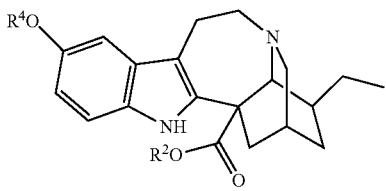

and/or its enantiomer, or a salt of each thereof wherein

R² is C₁-C₆ alkyl optionally substituted with 1-3 aryl groups and R⁴ is C₁-C₆ alkyl, C₁-C₆ alkyl substituted with 1-3, halo, C₁-C₆ alkoxy, phenyl, or substituted phenyl, where the substituted phenyl is substituted with 1-3, C₁-C₆ alkyl or C₁-C₆ alkoxy group, or R⁴ is a hydroxyl protecting group, comprising subjecting a compound of formula:

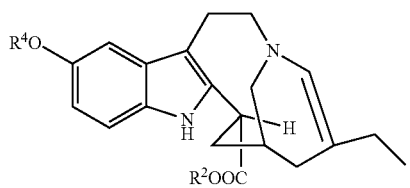

or a salt thereof to cyclization conditions to provide the compound of formula:

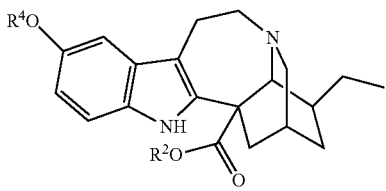

and its enantiomer, or a salt of each thereof.

The compound of formula:

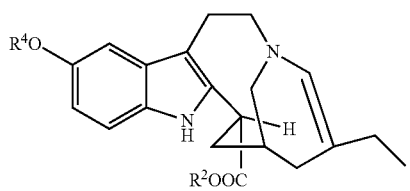

is refluxed in an inert solvent, preferably in absence of light. Suitable solvents include, without limitation benzene and the like. The refluxing is carried out for a period of time sufficient to form a substantial amount of the product.

In one embodiment, the process further comprises contacting the compound of formula:

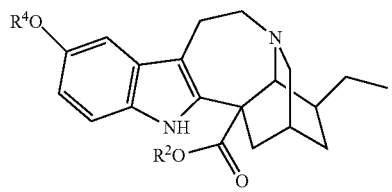

and/or its enantiomer (i.e., a racemic or scalemic mixture of the enantiomers), or a salt of each thereof, wherein R² and R⁴ are defined as in the process above, under reduction conditions to provide a compound of formula:

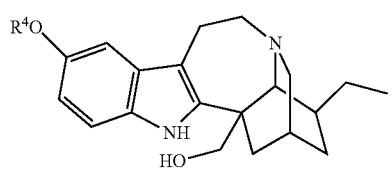

and/or its racemate, or a salt thereof. Suitable reduction conditions are well known the skilled artisan and include, contacting with a borohydride or and aluminum hydride, in an inert solvent such as ether or tetrahydrofuran, followed by aqueous work-up.

The compound of formula:

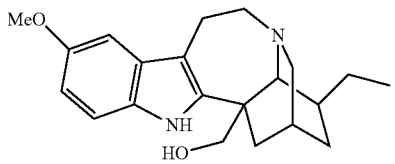 [SMILES: CCC1CC2CN3CCc4c([nH]c5ccc(OC)cc45)C(CO)(C2)C13]

along with its enantiomer, are esterified with a chiral carboxylic acid R³COOH to provide an ester compound of formula:

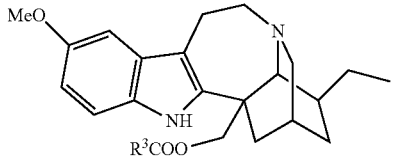

and its diastereomer. The diastereomeric forms of the ester compound can be separated, and the separated diastereomeric forms hydrolyzed to provide enantiomerically enriched:

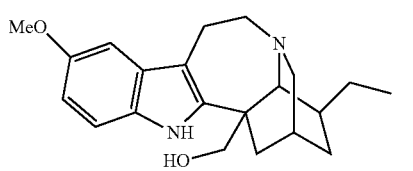

or

-continued

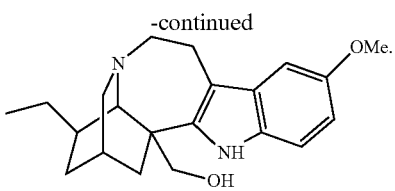

As will be apparent to the skilled artisan, the methods of making synthetic voacangine and other synthetic compounds as provided herein also require routine steps of separation and purification, which are performed by column chromatography, crystallization, and the like, as also well known to the skilled artisan. Enantiomerically enriched synthetic voacangine, or an enantiomerically enriched intermediate thereto or an enantiomerically enriched derivative thereof as utilized and provided herein is contemplated to be obtained, inter alia, by chiral chromatographic separation, and/or resolution via diastereomeric salt formation, and/or separation of diastereomeric derivatives. Chiral acids and bases suitable for resolving synthetic voacangine or an intermediate or derivative thereto will be well known to the skilled artisan.

EXAMPLES

These examples illustrate the conversion of resolved (−) and (+) voacangine to the corresponding (−) and (+) noribogaine.

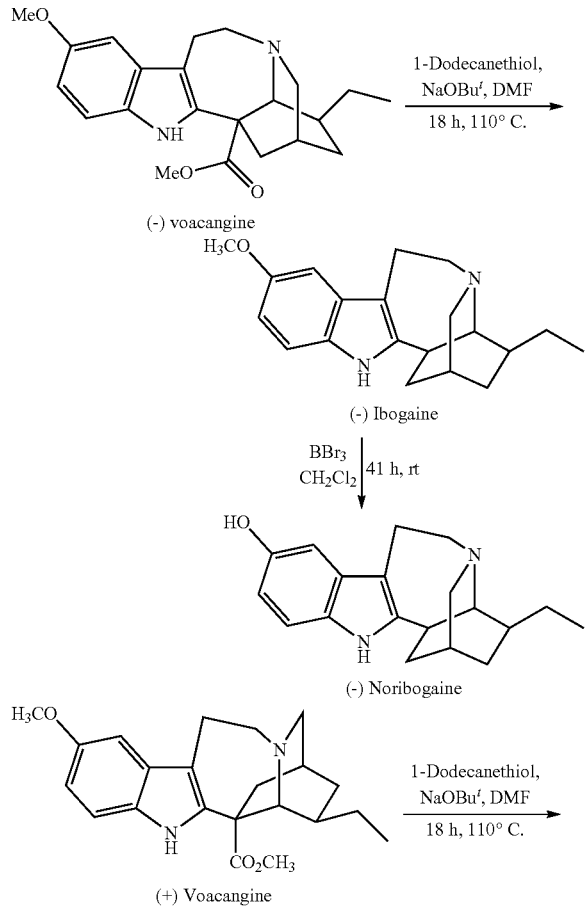

-continued

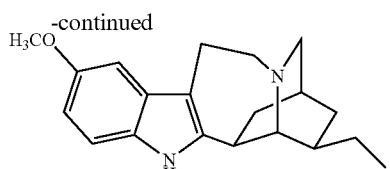

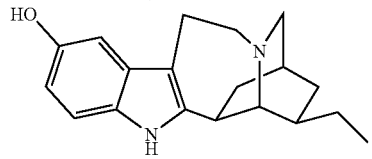

Resolved (+) voacangine (200 mg, 1 equivalent) and 1-dodecanethiol (1.5 equivalent) in dimethyl formamide (DMF, 1.2 mL) was added to a mixture of sodium tertiary butoxide (1.5 equivalent) in DMF (0.8 mL) at 100° C. and the reaction mixture stirred in the dark at 110-120° C. for 6 h and then at room temperature for about 12 h. Volatiles were removed in vacuum, and after aqueous work-up, (+) ibogaine was isolated by extraction with dichoromethane. The organic portion was washed with water and dried over $MgSO_4$. Volatiles were removed to provide ibogaine as a foamy solid (140 mg). A solution of ibogaine thus obtained, in dichloromethane (DCM, 1.4 mL), was added to a 1 molar $BBr_3$ (1.5 equivalent) solution in DCM at 0-5° C. over a 2 h period to provide a suspension, which was stirred at room temperature for 12 h. Then, the reaction mixture was cooled to 0-5° C. and MeOH (0.6 mL) was added to it drop wise over a period of 15 minutes and the resulting mixture stirred at room temperature for 12 h. Volatiles were removed in vacuum, and the residue was separated by column chromatography on silica gel using 5% $MeOH/CHCl_3$ as the eluent to obtain (+) noribogaine (70 mg) as a foamy solid. Specific rotations determined for the naturally occurring (−) enantiomers, and the synthetic (+) enantiomers made according to this invention are tabulated below, which demonstrate the stereochemistry and enantiomeric purity of the synthetic enantiomers prepared according to this invention.

| | Specific rotation | |
| --- | --- | --- |
| Enantiomer | Natural | Synthetic |
| Voacangine | −42°, c = 1, in chloroform | +41.3°, c = 1, in chloroform |
| Ibogaine | −48.5°, c = 1, in water | +47.9°, c = 1; in water |
| Noribogaine | −36.4°, c = 1, in water | +36.2°, c = 1, in water |

UTILITY (−) Voacangine has utility in preparing (−) noribogaine, which is useful for treating drug dependency and as an analgesic. See U.S. Pat. Nos. 6,348,456 7,220,737, supra. The voacangine derivatives provided here are also useful for preparing noribogaine. (+) Voacangine and (+) ibogaine is useful for preparing and (+) noribogaine. It is contemplated that (+) noribogaine has utility for treating pain and addiction in a manner similar to (−) noribogaine. It is further contemplated that derivatives of voacangine are useful for testing the the role of opioid receptors in overcoming pain.

What is claimed is:

1. (+) Voacangine, (+) ibogaine, or (+) noribogaine, which is present in a substantially enantiomerically enriched form.

2. (+) Voacangine present in a substantially enantiomerically enriched form.

3. (+) Ibogaine present in a substantially enantiomerically enriched form.

4. (+) Noribogaine present in a substantially enantiomerically enriched form.

* * * * *